US008074644B2

(12) United States Patent
Hale et al.

(10) Patent No.: US 8,074,644 B2
(45) Date of Patent: *Dec. 13, 2011

(54) METHOD OF FORMING AN AEROSOL FOR INHALATION DELIVERY

(75) Inventors: Ron L. Hale, Sandia Park, NM (US); Craig C. Hodges, Walnut Creek, CA (US); Peter M. Lloyd, Walnut Creek, CA (US); Daniel Mufson, Napa, CA (US); Daniel D. Rogers, Oakland, CA (US); Soonho Song, Hillsborough, CA (US); Martin J. Wensley, Los Gatos, CA (US); Daniel J. Myers, Mountain View, CA (US); Jeffrey A. McKinney, Lafayette, CA (US); Reynaldo J. Quintana, Redwood City, CA (US); Joshua D. Rabinowitz, Princeton, NJ (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 12/471,070

(22) Filed: May 22, 2009

(65) Prior Publication Data

US 2009/0229600 A1    Sep. 17, 2009

Related U.S. Application Data

(63) Continuation of application No. 10/146,088, filed on May 13, 2002, now Pat. No. 7,537,009, which is a continuation-in-part of application No. 10/057,198, filed on Oct. 26, 2001, now abandoned, and a continuation of application No. 10/057,197, filed on Oct. 26, 2001, now Pat. No. 7,766,013.

(60) Provisional application No. 60/296,225, filed on Jun. 5, 2001.

(51) Int. Cl.
*A61L 9/04* (2006.01)

(52) U.S. Cl. ............... 128/203.16; 128/200.14; 424/46

(58) Field of Classification Search ............ 128/200.16, 128/200.14, 200.19, 200.18, 203.25, 203.26, 128/204.14, 204.15, 204.16, 203.16, 203.17, 128/203.18; 424/25, 46
See application file for complete search history.

(56) References Cited

U.S. PATENT DOCUMENTS 1,239,634 A    9/1917    Stuart
(Continued)

FOREIGN PATENT DOCUMENTS

CA    2152684    1/1996
(Continued)

OTHER PUBLICATIONS

U.S. Appl. No. 11/687,466, filed Mar. 16, 2007, Zaffaroni et al.
(Continued)

*Primary Examiner* — Steven Douglas
(74) *Attorney, Agent, or Firm* — Swanson & Bratschun, L.L.C.

(57) ABSTRACT

The present invention relates to the inhalation delivery of aerosols containing small particles. Specifically, it relates to a method of forming an aerosol for use in inhalation therapy. In a method aspect of the present invention, a method of forming an aerosol for use in inhalation therapy is provided. The method involves the following steps: (a) heating a substrate coated with a composition comprising a drug at a rate greater than 1000° C./s, thereby forming an vapor; and, (b) allowing the vapor to cool, thereby forming an aerosol, which is used in inhalation therapy. In another method aspect of the present invention, a method of forming an aerosol for use in inhalation therapy is provided. The method involves the following steps: (a) heating a substrate coated with a composition comprising a drug to form a vapor, wherein the coated composition is in the form of a film less than 10μ thick; and, (b) allowing the vapor to cool, thereby forming an aerosol, which is used in inhalation therapy. In another method aspect of the present invention, a method of forming an aerosol for use in inhalation therapy is provided. The method involves the following steps: (a) heating a substrate coated with a composition comprising a drug to form a vapor in less than 100 milliseconds, wherein the vapor has a mass greater than 0.1 mg; and, (b) allowing the vapor to cool, thereby forming an aerosol, which is used in inhalation therapy.

14 Claims, 14 Drawing Sheets

U.S. PATENT DOCUMENTS

| | | |
|---|---|---|
| 1,535,486 A | 4/1925 | Lundy |
| 1,803,334 A | 5/1931 | Lehmann |
| 1,864,980 A | 6/1932 | Curran |
| 2,084,299 A | 6/1937 | Borden |
| 2,086,140 A | 7/1937 | Ernst |
| 2,230,753 A | 2/1941 | Klavehn et al. |
| 2,230,754 A | 2/1941 | Klavehn et al. |
| 2,243,669 A | 5/1941 | Clyne |
| 2,309,846 A | 2/1943 | Holm |
| 2,469,656 A | 5/1949 | Lienert |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |
| 2,902,484 A | 9/1959 | Horclois |
| 3,043,977 A | 7/1962 | Morowitz |
| 3,080,624 A | 3/1963 | Webber, III |
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,282,729 A | 11/1966 | Richardson et al. |
| 3,296,249 A | 1/1967 | Bell |
| 3,299,185 A | 1/1967 | Oda et al. |
| 3,371,085 A | 2/1968 | Reeder et al. |
| 3,393,197 A | 7/1968 | Pachter |
| 3,433,791 A | 3/1969 | Bentley et al. |
| 3,560,607 A | 2/1971 | Hartley et al. |
| 3,701,782 A | 10/1972 | Hester |
| 3,749,547 A | 7/1973 | Gregory et al. |
| 3,763,347 A | 10/1973 | Whitaker et al. |
| 3,773,995 A | 11/1973 | Pachter et al. |
| 3,831,606 A | 8/1974 | Damani |
| 3,847,650 A | 11/1974 | Gregory et al. |
| 3,864,326 A | 2/1975 | Babington |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick et al. |
| 4,020,379 A | 4/1977 | Manning |
| 4,045,156 A | 8/1977 | Chu et al. |
| 4,079,742 A | 3/1978 | Rainer et al. |
| 4,104,210 A | 8/1978 | Coran et al. |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,198,200 A | 4/1980 | Fonda et al. |
| RE30,285 E | 5/1980 | Babington |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,346,059 A | 8/1982 | Spector |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,523,589 A | 6/1985 | Krauser |
| 4,556,539 A | 12/1985 | Spector |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III et al. |
| 4,683,231 A | 7/1987 | Glassman |
| 4,693,868 A | 9/1987 | Katsuda et al. |
| 4,708,151 A | 11/1987 | Shelar |
| 4,714,082 A | 12/1987 | Banerjee et al. |
| 4,722,334 A | 2/1988 | Blackmer et al. |
| 4,734,560 A | 3/1988 | Bowen |
| 4,735,217 A | 4/1988 | Gerth et al. |
| 4,735,358 A | 4/1988 | Morita et al. |
| 4,753,758 A | 6/1988 | Miller |
| 4,755,508 A | 7/1988 | Bock et al. |
| 4,756,318 A | 7/1988 | Clearman et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,852,561 A | 8/1989 | Sperry |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,892,109 A | 1/1990 | Strubel |
| 4,895,719 A | 1/1990 | Radhakrishnan et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A | 5/1990 | Brooks et al. |
| 4,924,883 A | 5/1990 | Perfetti et al. |
| 4,928,714 A | 5/1990 | Shannon |
| 4,935,624 A | 6/1990 | Henion et al. |
| 4,941,483 A | 7/1990 | Ridings et al. |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz et al. |
| 4,968,885 A | 11/1990 | Willoughby |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman et al. |
| 5,020,548 A | 6/1991 | Farrier et al. |
| 5,027,836 A | 7/1991 | Shannon et al. |
| 5,033,483 A | 7/1991 | Clearman et al. |
| 5,038,769 A | 8/1991 | Krauser |
| 5,042,509 A | 8/1991 | Banerjee et al. |
| 5,049,389 A | 9/1991 | Radhakrishnan |
| 5,060,666 A | 10/1991 | Clearman et al. |
| 5,060,667 A | 10/1991 | Strubel |
| 5,060,671 A | 10/1991 | Counts et al. |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,093,894 A | 3/1992 | Deevi et al. |
| 5,095,921 A | 3/1992 | Losee et al. |
| 5,099,861 A | 3/1992 | Clearman et al. |

| Patent | Date | Inventor |
|---|---|---|
| 5,105,831 A | 4/1992 | Banerjee et al. |
| 5,109,180 A | 4/1992 | Boultinghouse et al. |
| 5,112,598 A | 5/1992 | Biesalski |
| 5,118,494 A | 6/1992 | Schultz et al. |
| 5,119,834 A | 6/1992 | Shannon et al. |
| 5,126,123 A | 6/1992 | Johnson |
| 5,133,368 A | 7/1992 | Neumann et al. |
| 5,135,009 A | 8/1992 | Muller et al. |
| 5,137,034 A | 8/1992 | Perfetti et al. |
| 5,144,962 A | 9/1992 | Counts et al. |
| 5,146,915 A | 9/1992 | Montgomery |
| 5,149,538 A | 9/1992 | Granger et al. |
| 5,156,170 A | 10/1992 | Clearman et al. |
| 5,160,664 A | 11/1992 | Liu |
| 5,164,740 A | 11/1992 | Ivri |
| 5,166,202 A | 11/1992 | Schweizer |
| 5,167,242 A | 12/1992 | Turner et al. |
| 5,177,071 A | 1/1993 | Freidinger et al. |
| 5,179,966 A | 1/1993 | Losee et al. |
| 5,186,164 A | 2/1993 | Raghuprasad |
| 5,192,548 A | 3/1993 | Velasquez et al. |
| 5,224,498 A | 7/1993 | Deevi et al. |
| 5,226,411 A | 7/1993 | Levine |
| 5,229,120 A | 7/1993 | DeVincent |
| 5,229,382 A | 7/1993 | Chakrabarti et al. |
| 5,240,922 A | 8/1993 | O'Neill |
| 5,249,586 A | 10/1993 | Morgan et al. |
| 5,255,674 A | 10/1993 | Oftedal et al. |
| 5,261,424 A | 11/1993 | Sprin et al. |
| 5,264,433 A | 11/1993 | Sato et al. |
| 5,269,327 A | 12/1993 | Counts et al. |
| 5,284,133 A | 2/1994 | Burns et al. |
| 5,285,798 A | 2/1994 | Banerjee et al. |
| 5,292,499 A | 3/1994 | Evans et al. |
| 5,322,075 A | 6/1994 | Deevi et al. |
| 5,333,106 A | 7/1994 | Lanpher et al. |
| 5,345,951 A | 9/1994 | Serrano et al. |
| 5,357,984 A | 10/1994 | Farrier et al. |
| 5,363,842 A | 11/1994 | Mishelevich et al. |
| 5,364,838 A | 11/1994 | Rubsamen |
| 5,366,770 A | 11/1994 | Wang |
| 5,372,148 A | 12/1994 | McCafferty et al. |
| 5,376,386 A | 12/1994 | Ganderton et al. |
| 5,388,574 A | 2/1995 | Ingebrethsen |
| 5,391,081 A | 2/1995 | Lampotang et al. |
| 5,399,574 A | 3/1995 | Robertson et al. |
| 5,400,808 A | 3/1995 | Turner et al. |
| 5,400,969 A | 3/1995 | Keene |
| 5,402,517 A | 3/1995 | Gillett et al. |
| 5,408,574 A | 4/1995 | Deevi et al. |
| 5,436,230 A | 7/1995 | Soudant et al. |
| 5,451,408 A | 9/1995 | Mezei et al. |
| 5,455,043 A | 10/1995 | Fischel-Ghodsian |
| 5,456,247 A | 10/1995 | Shilling et al. |
| 5,456,677 A | 10/1995 | Spector |
| 5,457,100 A | 10/1995 | Daniel |
| 5,457,101 A | 10/1995 | Greenwood et al. |
| 5,459,137 A | 10/1995 | Andrasi et al. |
| 5,462,740 A | 10/1995 | Evenstad et al. |
| 5,468,936 A | 11/1995 | Deevi et al. |
| 5,479,948 A | 1/1996 | Counts et al. |
| 5,501,236 A | 3/1996 | Hill et al. |
| 5,505,214 A | 4/1996 | Collins et al. |
| 5,507,277 A | 4/1996 | Rubsamen et al. |
| 5,511,726 A | 4/1996 | Greenspan et al. |
| 5,519,019 A | 5/1996 | Andrasi et al. |
| 5,525,329 A | 6/1996 | Snyder et al. |
| 5,537,507 A | 7/1996 | Mariner et al. |
| 5,538,020 A | 7/1996 | Farrier et al. |
| 5,540,959 A | 7/1996 | Wang |
| 5,543,434 A | 8/1996 | Weg |
| 5,544,646 A | 8/1996 | Lloyd et al. |
| 5,564,442 A | 10/1996 | MacDonald et al. |
| 5,565,148 A | 10/1996 | Pendergrass |
| 5,577,156 A | 11/1996 | Costello |
| 5,584,701 A | 12/1996 | Lampotang et al. |
| 5,586,550 A | 12/1996 | Ivri et al. |
| 5,591,409 A | 1/1997 | Watkins |
| 5,592,934 A | 1/1997 | Thwaites |
| 5,593,792 A | 1/1997 | Farrier et al. |
| 5,605,146 A | 2/1997 | Sarela |
| 5,605,897 A | 2/1997 | Beasley, Jr. et al. |
| 5,607,691 A | 3/1997 | Hale et al. |
| 5,613,504 A | 3/1997 | Collins et al. |
| 5,613,505 A | 3/1997 | Campbell et al. |
| 5,619,984 A | 4/1997 | Hodson et al. |
| 5,622,944 A | 4/1997 | Hale et al. |
| 5,627,178 A | 5/1997 | Chakrabarti et al. |
| 5,649,554 A | 7/1997 | Sprinkel |
| 5,655,523 A | 8/1997 | Hodson et al. |
| 5,656,255 A | 8/1997 | Jones |
| 5,660,166 A | 8/1997 | Lloyd et al. |
| 5,666,977 A | 9/1997 | Higgins et al. |
| 5,690,809 A | 11/1997 | Subramaniam et al. |
| 5,694,919 A | 12/1997 | Rubsamen et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,767,117 A | 6/1998 | Moskowitz |
| 5,769,621 A | 6/1998 | Early et al. |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,855,564 A | 1/1999 | Ruskewicz |
| 5,855,913 A | 1/1999 | Hanes et al. |
| 5,865,185 A | 2/1999 | Collins et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,904,900 A | 5/1999 | Bleuse et al. |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang et al. |
| 5,934,272 A | 8/1999 | Lloyd et al. |
| 5,934,289 A | 8/1999 | Watkins et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda et al. |
| 5,971,951 A | 10/1999 | Ruskewicz |
| 5,985,309 A | 11/1999 | Edwards et al. |
| 5,993,805 A | 11/1999 | Sutton et al. |
| 6,004,516 A | 12/1999 | Rasouli et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,013,050 A | 1/2000 | Bellhouse et al. |
| 6,014,969 A | 1/2000 | Lloyd et al. |
| 6,014,970 A | 1/2000 | Ivri et al. |

| Patent Number | Date | Inventor |
|---|---|---|
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| 6,053,176 A | 4/2000 | Adams et al. |
| RE36,744 E | 6/2000 | Goldberg |
| 6,085,026 A | 7/2000 | Hammons et al. |
| 6,089,857 A | 7/2000 | Matsuura et al. |
| 6,090,212 A | 7/2000 | Mahawili |
| 6,090,403 A | 7/2000 | Block et al. |
| 6,095,134 A | 8/2000 | Sievers et al. |
| 6,095,153 A | 8/2000 | Kessler et al. |
| 6,098,620 A | 8/2000 | Lloyd et al. |
| 6,102,036 A | 8/2000 | Slutsky et al. |
| 6,113,795 A | 9/2000 | Subramaniam et al. |
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,570 A | 10/2000 | Schuster et al. |
| 6,133,327 A | 10/2000 | Kimura et al. |
| 6,135,369 A | 10/2000 | Prendergast et al. |
| 6,136,295 A | 10/2000 | Edwards et al. |
| 6,138,683 A | 10/2000 | Hersh et al. |
| 6,140,323 A | 10/2000 | Ellinwood, Jr. et al. |
| 6,143,277 A | 11/2000 | Ashurst et al. |
| 6,143,746 A | 11/2000 | Daugan et al. |
| 6,149,892 A | 11/2000 | Britto |
| 6,155,268 A | 12/2000 | Takeuchi |
| 6,158,431 A | 12/2000 | Poole |
| 6,167,880 B1 | 1/2001 | Gonda et al. |
| 6,178,969 B1 | 1/2001 | St. Charles |
| 6,234,167 B1 | 5/2001 | Cox et al. |
| 6,241,969 B1 | 6/2001 | Saidi et al. |
| 6,250,301 B1 | 6/2001 | Pate |
| 6,255,334 B1 | 7/2001 | Sands |
| 6,263,872 B1 | 7/2001 | Schuster et al. |
| 6,264,922 B1 | 7/2001 | Wood et al. |
| 6,284,287 B1 | 9/2001 | Sarlikiotis et al. |
| 6,299,900 B1 | 10/2001 | Reed et al. |
| 6,300,710 B1 | 10/2001 | Nakamori |
| 6,306,431 B1 | 10/2001 | Zhang et al. |
| 6,309,668 B1 | 10/2001 | Bastin et al. |
| 6,309,986 B1 | 10/2001 | Flashinski et al. |
| 6,313,176 B1 | 11/2001 | Ellinwood, Jr. et al. |
| 6,325,475 B1 | 12/2001 | Hayes et al. |
| 6,376,550 B1 | 4/2002 | Raber et al. |
| 6,390,453 B1 | 5/2002 | Frederickson et al. |
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,461,591 B1 | 10/2002 | Keller et al. |
| 6,491,233 B2 | 12/2002 | Nichols |
| 6,501,052 B2 | 12/2002 | Cox et al. |
| 6,506,762 B1 | 1/2003 | Horvath et al. |
| 6,514,482 B1 | 2/2003 | Bartus et al. |
| 6,516,796 B1 | 2/2003 | Cox et al. |
| 6,557,552 B1 | 5/2003 | Cox et al. |
| 6,561,186 B2 | 5/2003 | Casper et al. |
| 6,568,390 B2 | 5/2003 | Nichols et al. |
| 6,591,839 B2 | 7/2003 | Meyer et al. |
| 6,632,047 B2 | 10/2003 | Vinegar et al. |
| 6,648,950 B2 | 11/2003 | Lee et al. |
| 6,671,945 B2 | 1/2004 | Gerber et al. |
| 6,680,668 B2 | 1/2004 | Gerber et al. |
| 6,681,769 B2 | 1/2004 | Sprinkel et al. |
| 6,681,998 B2 | 1/2004 | Sharpe et al. |
| 6,682,716 B2 | 1/2004 | Hodges et al. |
| 6,688,313 B2 | 2/2004 | Wrenn et al. |
| 6,694,975 B2 | 2/2004 | Schuster et al. |
| 6,701,921 B2 | 3/2004 | Sprinkel et al. |
| 6,701,922 B2 | 3/2004 | Hindle et al. |
| 6,715,487 B2 | 4/2004 | Nichols et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,728,478 B2 | 4/2004 | Cox et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,772,757 B2 | 8/2004 | Sprinkel, Jr. et al. |
| 6,776,978 B2 | 8/2004 | Rabinowitz et al. |
| 6,779,520 B2 | 8/2004 | Genova et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Ron et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |

| | | |
|---|---|---|
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 2001/0020147 A1 | 9/2001 | Staniforth et al. |
| 2001/0042546 A1 | 11/2001 | Umeda et al. |
| 2002/0031480 A1 | 3/2002 | Peart et al. |
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0078955 A1 | 6/2002 | Nichols et al. |
| 2002/0086852 A1 | 7/2002 | Cantor |
| 2002/0097139 A1 | 7/2002 | Gerber et al. |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0032638 A1 | 2/2003 | Kim et al. |
| 2003/0033055 A1 | 2/2003 | McRae et al. |
| 2003/0049025 A1 | 3/2003 | Neumann et al. |
| 2003/0051728 A1 | 3/2003 | Lloyd et al. |
| 2003/0062042 A1 | 4/2003 | Wensley et al. |
| 2003/0106551 A1 | 6/2003 | Sprinkel et al. |
| 2003/0118512 A1 | 6/2003 | Shen |
| 2003/0121906 A1 | 7/2003 | Abbott et al. |
| 2003/0131843 A1 | 7/2003 | Lu |
| 2003/0132219 A1 | 7/2003 | Cox et al. |
| 2003/0138508 A1 | 7/2003 | Novack et al. |
| 2003/0156829 A1 | 8/2003 | Cox et al. |
| 2004/0009128 A1 | 1/2004 | Rabinowitz et al. |
| 2004/0016427 A1 | 1/2004 | Byron et al. |
| 2004/0035409 A1 | 2/2004 | Harwig et al. |
| 2004/0055504 A1 | 3/2004 | Lee et al. |
| 2004/0081624 A1 | 4/2004 | Nguyen et al. |
| 2004/0096402 A1 | 5/2004 | Hodges et al. |
| 2004/0099266 A1 | 5/2004 | Cross et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0105819 A1 | 6/2004 | Hale et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2005/0268911 A1 | 12/2005 | Cross et al. |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0193788 A1 | 8/2006 | Hale et al. |
| 2006/0257329 A1 | 11/2006 | Rabinowitz et al. |
| 2006/0280692 A1 | 12/2006 | Rabinowitz et al. |
| 2007/0028916 A1 | 2/2007 | Hale et al. |
| 2007/0031340 A1 | 2/2007 | Hale et al. |
| 2007/0122353 A1 | 5/2007 | Hale et al. |
| 2007/0140982 A1 | 6/2007 | Every et al. |
| 2007/0286816 A1 | 12/2007 | Hale et al. |
| 2008/0110872 A1 | 5/2008 | Hale et al. |
| 2008/0175796 A1 | 7/2008 | Rabinowitz et al. |
| 2008/0216828 A1 | 9/2008 | Wensley |
| 2008/0299048 A1 | 12/2008 | Hale et al. |
| 2008/0306285 A1 | 12/2008 | Hale et al. |
| 2008/0311176 A1 | 12/2008 | Hale et al. |
| 2009/0062254 A1 | 3/2009 | Hale et al. |
| 2009/0071477 A1 | 3/2009 | Hale et al. |

FOREIGN PATENT DOCUMENTS

| | | |
|---|---|---|
| CN | 1082365 | 2/1994 |
| CN | 1176075 | 3/1998 |
| DE | 198 54 007 | 5/2000 |
| EP | 0 039 369 | 11/1981 |
| EP | 0 274 431 | 7/1988 |
| EP | 0 277 519 | 8/1988 |
| EP | 0 358 114 | 3/1990 |
| EP | 0 430 559 | 6/1991 |
| EP | 0 492 485 | 7/1992 |
| EP | 0 606 486 | 7/1994 |
| EP | 0 734 719 | 2/1996 |
| EP | 0 967 214 | 12/1999 |
| EP | 1 080 720 | 3/2001 |
| EP | 1 177 793 | 2/2002 |
| EP | 0 808 635 B1 | 7/2003 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| HU | 200105 B | 10/1988 |
| HU | 219392 B | 6/1993 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/36574 | 10/1997 |
| WO | WO 97/40819 | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/16419 | 4/1999 |
| WO | WO 99/24433 | 5/1999 |
| WO | WO 99/37347 | 7/1999 |
| WO | WO 99/37625 | 7/1999 |
| WO | WO 99/44664 | 9/1999 |

| | | |
|---|---|---|
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/43801 | 6/2001 |
| WO | WO 01/95903 | 12/2001 |
| WO | WO 02/00198 | 1/2002 |
| WO | WO 02/24158 | 3/2002 |
| WO | WO 02/051466 | 7/2002 |
| WO | WO 02/056866 | 7/2002 |
| WO | WO 02/094234 | 11/2002 |
| WO | WO 02/098389 | 12/2002 |
| WO | WO 03/037412 | 5/2003 |

OTHER PUBLICATIONS

U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/352,582, filed Jan. 12, 2009, Hale et al.
U.S. Appl. No. 12/413,339, filed Mar. 27, 2009, Rabinowitz et al.
U.S. Appl. No. 12/474,680, filed May 29, 2009, Cross et al.
U.S. Appl. No. 12/485,704, filed Jun. 16, 2009, Damani et al.
U.S. Appl. No. 12/490,102, filed Jun. 23, 2009, Hale et al.
Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 4, 2003 with respect to U.S. Appl. No. 10/057,198.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Aug. 13, 2003 with respect to U.S. Appl. No. 10/153,313.
Office Action mailed Mar. 8, 2005 with respect to U.S. Appl. No. 10/718,982.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER, pp. 1-110.
Bennett, R. L. et al. (1981). "Patient-Controlled Analgesia: A New Concept of Postoperative Pain Relief," Annual Surg. 195(6):700-705.
Benowitz (1994). "Individual Differences in Nicotine Kinetics and Metabolism in Humans," NIDA Research Monography, 2 pages.
BP: Chemicals Products-Barrier Resins (1999). located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," Journal of Pharmaceutical Sciences. 89(6):724-731.
Campbell, Fiona A. et al. (2001) "Are cannabinoids an effective and safe treatment option in the management of pain? A qualitative systemic review," BMJ, 323 pp. 1-6.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral DELTA 9—tetrahydrocannabinol: Dose response analysis and receptor identification" Journal of Pharmacology and Experimental Therapeutics vol. 289 (2): 859-867.
Clark, A. and Byron, P. (1986). "Dependence of Pulmonary Absorption Kinetics on Aerosol Particle Size," Z. Erkrank. 166:13-24.
Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422.
Darquenne, C. et al. (1997). "Aerosol Dispersion in Human Lung: Comparison Between Numerical Simulations and Experiments for Bolus Tests," American Physiological Society. 966-974.
Database Biosis "Online!" Biosciences Information Service, Philadelphia, PA 1979, Knight, V. et al., "Amantadine aerosol in humans", database accession No. PREV 198069035552 abstract, & Antimicrobial Agents and Chemotherapy 16(5):572-578.
Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; Class B07, AN 1989-297792 AP002230849 & JP 01 221313 (NIPPON CREATE 1(K), Sep. 4, 1989, abstract.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Drugs Approved by the FDA—Drug Name: Nicotrol Inhaler (2000) located at <http://www.centerwatch.com/patient/drugs/dru202.html> (Visited on Aug. 2, 2001), 2 pages.
Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.

Finlay, W. H. (2001). "The Mechanics of Inhaled Pharmaceutical Aerosols", Academic Press: San Diego Formula 2.39. pp. 3-14 (Table of Contents). pp. v-viii.

Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.

Graves, D. A. et al. (1983). "Patient-Controlled Analgesia" Annals of Internal Medicine. 99:360-366.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 µm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.

James, A.C. et al., (1991). "The Respiratory Tract Deposition Model Proposed by the ICRP Task Group," Radiation Protection Dosimetry, 38(1/3):159-165.

Kim, M. H. and Patel, D.V. (1994). "'BOP' As a Reagent for Mild and Efficient Preparation of Esters," Tet. Letters 35:5603-5606.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. (Mar. 2000). ACS Conference—San Francisco—Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Poochikian, G. and Bertha, C.M. (2000). "Inhalation Drug Product Excipient Controls: Significance and Pitfalls," Resp. Drug Deliv. VII: 109-115.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

Vapotronics, Inc. (1998) located at http://www.vapotronics.com.au/banner.htm., 11 pages, (visited on Jun. 5, 2000).

Vaughan, N. P. (1990). "The Generation of Monodisperse Fibres of Caffeine" J. Aerosol Sci. 21(3): 453-462.

Ward, M. E. MD, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

Number Concentration vs Time for Number Concentration to Halve

Time (seconds)

Coagulation Coefficient vs. Particle Size

Particle Size (nm)

Vapor Pressure vs Temperature

Blood Levels vs Time; IV and Inhaled Fentanyl

Actual vs Calculated Particle Diameter (MMD) for Number Concentration of $1 \times 10^9$/cc Actual vs Calculated Particle Diameter (MMD) for Number Concentration of $0.5 \times 10^9$/cc

Fig. 29

Ratio of Vaporized Compound to Volume of Mixing Gas vs. Particle Diameter

METHOD OF FORMING AN AEROSOL FOR INHALATION DELIVERY

This application is a continuation of U.S. patent application Ser. No. 10/146,088, entitled "Method Of Forming An Aerosol For Inhalation Delivery", filed May 13, 2002, which is a continuation-in-part of U.S. patent application Ser. No. 10/057,198 entitled "Method and Device for Delivering a Physiologically Active Compound," filed Oct. 26, 2001, Lloyd et al. and of U.S. patent application Ser. No. 10/057,197 entitled "Aerosol Generating Device and Method," filed Oct. 26, 2001, Wensley et al. This application further claims priority to U.S. provisional application Ser. No. 60/296,225 entitled "Aerosol Generating Device and Method," filed Jun. 5, 2001, Wensley et al. The entire disclosures of which are hereby incorporated by reference. Any disclaimer that may have occurred during the prosecution of the above-referenced applications is hereby expressly rescinded, and reconsideration of all relevant art is respectfully requested.

FIELD OF THE INVENTION

The present invention relates to the inhalation delivery of aerosols containing small particles. Specifically, it relates to a method of forming an aerosol for use in inhalation therapy.

BACKGROUND OF THE INVENTION

Currently, there are a number of approved devices for the inhalation delivery of drugs, including dry powder inhalers, nebulizers, and pressurized metered dose inhalers. The aerosols produced by the devices, however, typically contain an excipient.

It is desirable to provide a method that can produce aerosols in the absence of excipients. The provision of such a device is an object of the present invention.

SUMMARY OF THE INVENTION

The present invention relates to the inhalation delivery of aerosols containing small particles. Specifically, it relates to a method of forming an aerosol for use in inhalation therapy.

In a method aspect of the present invention, a method of forming an aerosol for use in inhalation therapy is provided. The method involves the following steps: (a) heating a substrate coated with a composition comprising a drug at a rate greater than 1000° C./s, thereby forming an vapor; and, (b) allowing the vapor to cool, thereby forming an aerosol, which is used in inhalation therapy. Preferably, the substrate is heated at a rate greater than 2,000° C./s, 5,000° C./s, 7,500° C./s, or 10,000° C./s.

In certain cases, the substrate is heated at a rate of about 2,000° C./s.

Typically, the composition is coated on the substrate as a film that is less than 10μ thick. Preferably, the film thickness is less than 5μ, 4μ, 3μ, 2μ, or 1μ thick.

Typically, the composition is coated on the substrate as a film that is between 10μ and 10 nm in thickness. Preferably, the film thickness is between 5μ and 10 nm, 4μ and 10 nm, 3μ and 10 nm, 2μ and 10 nm, or 1μ and 10 nm in thickness.

Typically, greater than 0.1 mg of the composition is vaporized in less than 100 milliseconds from the start of heating. Preferably, 0.25 mg, 0.5 mg, 0.75 mg, or 1 mg of the composition is vaporized in less than 100 milliseconds from the start of heating. More preferably, the same amount of composition list above is vaporized in less than 75 milliseconds, 50 milliseconds, 25 milliseconds, or 10 milliseconds from the start of heating.

Typically, the formed aerosol is greater than 10 percent by weight of the drug. Preferably, it is greater than 20 percent by weight of the drug. More preferably, it is greater than 30 percent, 40 percent, 50 percent, 60 percent, 70 percent, 80 percent, 90 percent, 95 percent or 97 percent by weight of the drug.

Typically, the formed aerosol contains less than 10 percent by weight of drug decomposition products. Preferably, it contains less than 5 percent by weight of drug decomposition products. More preferably, it contains less than 3 percent, 2 percent or 1 percent by weight of drug decomposition products.

Typically, the drug has a decomposition index less than 0.15. Preferably, the drug has a decomposition index less than 0.10. More preferably, the drug has a decomposition index less than 0.05.

Typically, the drug of the composition is of one of the following classes: antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesics and stimulants.

Typically, where the drug is an antibiotic, it is selected from one of the following compounds: cefmetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

Typically, where the drug is an anticonvulsant, it is selected from one of the following compounds: gabapentin, tiagabine, and vigabatrin.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron methanesulfonate, droperidol, granisetron, hyoscine, lorazepam, metoclopramide, metopimazine, ondansetron, perphenazine, promethazine, prochlorperazine, scopolamine, triethylperazine, trifluoperazine, triflupromazine, trimethobenzamide, tropisetron, domeridone, and palonosetron.

Typically, where the drug is an antihistamine, it is selected from one of the following compounds: azatadine, brompheniramine, chlorpheniramine, clemastine, cyproheptadine, dexmedetomidine, diphenhydramine, doxylamine, hydroxyzine, cetrizine, fexofenadine, loratidine, and promethazine.

Typically, where the drug is an antiparkisonian drug, it is selected one of the following compounds: amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Typically, where the drug is an antipsychotic, it is selected from one of the following compounds: acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, butaclamol, clozapine, melperone, olanzapine, quetiapine, and risperidone.

Typically, where the drug is an anxiolytic, it is selected from one of the following compounds: mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Typically, where the drug is a drug for erectile dysfunction, it is selected from one of the following compounds: cialis (IC351), sildenafil, vardenafil, apomorphine, apomorphine diacetate, phentolamine, and yohimbine.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a drug for the treatment of alcoholism, it is selected from one of the following compounds: naloxone, naltrexone, and disulfuram.

Typically, where the drug is a drug for the treatment of addiction it is buprenorphine.

Typically, where the drug is a muscle relaxant, it is selected from one of the following compounds: baclofen, cyclobenzaprine, orphenadrine, quinine, and tizanidine.

Typically, where the drug is a nonsteroidal anti-inflammatory, it is selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papavereturn, pethidine, pentazocine, phenazocine, remifentanil, sufentanil, and tramadol.

Typically, where the drug is an other analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is a stimulant, it is selected from one of the following compounds: amphetamine, brucine, caffeine, dexfenfluramine, dextroamphetamine, ephedrine, fenfluramine, mazindol, methyphenidate, pemoline, phentermine, and sibutramine.

In another method aspect of the present invention, a method of forming an aerosol for use in inhalation therapy is provided. The method involves the following steps: (a) heating a substrate coated with a composition comprising a drug to form a vapor, wherein the coated composition is in the form of a film less than 10μ thick; and, (b) allowing the vapor to cool, thereby forming an aerosol, which is used in inhalation therapy. Preferably, the film thickness is less than 5μ, 4μ, 3μ, 2μ, or 1μ thick.

Typically, the composition is coated on the substrate as a film that is between 10μ and 10 nm in thickness. Preferably, the film thickness is between 5μ and 10 nm, 4μ and 10 nm, 3μ and 10 nm, 2μ and 10 nm, or 1μ and 10 nm in thickness.

Typically, greater than 0.1 mg of the composition is vaporized in less than 100 milliseconds from the start of heating. Preferably, 0.25 mg, 0.5 mg, 0.75 mg, or 1 mg of the composition is vaporized in less than 100 milliseconds from the start of heating. More preferably, the same amount of composition list above is vaporized in less than 75 milliseconds, 50 milliseconds, 25 milliseconds, or 10 milliseconds from the start of heating.

Typically, the formed aerosol is greater than 10 percent by weight of the drug. Preferably, it is greater than 20 percent by weight of the drug. More preferably, it is greater than 30 percent, 40 percent, 50 percent, 60 percent, 70 percent, 80 percent, 90 percent, 95 percent or 97 percent by weight of the drug.

Typically, the formed aerosol contains less than 10 percent by weight of drug decomposition products. Preferably, it contains less than 5 percent by weight of drug decomposition products. More preferably, it contains less than 3 percent, 2 percent or 1 percent by weight of drug decomposition products.

Typically, the drug has a decomposition index less than 0.15. Preferably, the drug has a decomposition index less than 0.10. More preferably, the drug has a decomposition index less than 0.05.

Typically, the drug of the composition is of one of the following classes: antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesics and stimulants.

Typically, where the drug is an antibiotic, it is selected from one of the following compounds: cefmetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

Typically, where the drug is an anticonvulsant, it is selected from one of the following compounds: gabapentin, tiagabine, and vigabatrin.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron methanesulfonate, droperidol, granisetron, hyoscine, lorazepam, metoclopramide, metopimazine, ondansetron, perphenazine, promethazine, prochlorperazine, scopolamine, triethylperazine, trifluoperazine, triflupromazine, trimethobenzamide, tropisetron, domeridone, and palonosetron.

Typically, where the drug is an antihistamine, it is selected from one of the following compounds: azatadine, brompheniramine, chlorpheniramine, clemastine, cyproheptadine, dexmedetomidine, diphenhydramine, doxylamine, hydroxyzine, cetrizine, fexofenadine, loratidine, and promethazine.

Typically, where the drug is an antiparkisonian drug, it is selected one of the following compounds: amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Typically, where the drug is an antipsychotic, it is selected from one of the following compounds: acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, butaclamol, clozapine, melperone, olanzapine, quetiapine, and risperidone.

Typically, where the drug is an anxiolytic, it is selected from one of the following compounds: mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Typically, where the drug is a drug for erectile dysfunction, it is selected from one of the following compounds: cialis (IC351), sildenafil, vardenafil, apomorphine, apomorphine diacetate, phentolamine, and yohimbine.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a drug for the treatment of alcoholism, it is selected from one of the following compounds: naloxone, naltrexone, and disulfuram.

Typically, where the drug is a drug for the treatment of addiction it is buprenorphine.

Typically, where the drug is a muscle relaxant, it is selected from one of the following compounds: baclofen, cyclobenzaprine, orphenadrine, quinine, and tizanidine.

Typically, where the drug is a nonsteroidal anti-inflammatory, it is selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papavereturn, pethidine, pentazocine, phenazocine, remifentanil, sufentanil, and tramadol.

Typically, where the drug is an other analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is a stimulant, it is selected from one of the following compounds: amphetamine, brucine, caffeine, dexfenfluramine, dextroamphetamine, ephedrine, fenfluramine, mazindol, methyphenidate, pemoline, phentermine, and sibutramine.

In another method aspect of the present invention, a method of forming an aerosol for use in inhalation therapy is provided. The method involves the following steps: (a) heating a substrate coated with a composition comprising a drug to form a vapor in less than 100 milliseconds, wherein the vapor has a mass greater than 0.1 mg; and, (b) allowing the vapor to cool, thereby forming an aerosol, which is used in inhalation therapy. Preferably, 0.25 mg, 0.5 mg, 0.75 mg, or 1 mg of the composition is vaporized in less than 100 milliseconds from the start of heating. More preferably, the same amount of composition list above is vaporized in less than 75 milliseconds, 50 milliseconds, 25 milliseconds, or 10 milliseconds from the start of heating.

Typically, the formed aerosol is greater than 10 percent by weight of the drug. Preferably, it is greater than 20 percent by weight of the drug. More preferably, it is greater than 30 percent, 40 percent, 50 percent, 60 percent, 70 percent, 80 percent, 90 percent, 95 percent or 97 percent by weight of the drug.

Typically, the formed aerosol contains less than 10 percent by weight of drug decomposition products. Preferably, it contains less than 5 percent by weight of drug decomposition products. More preferably, it contains less than 3 percent, 2 percent or 1 percent by weight of drug decomposition products.

Typically, the drug has a decomposition index less than 0.15. Preferably, the drug has a decomposition index less than 0.10. More preferably, the drug has a decomposition index less than 0.05.

Typically, the drug of the composition is of one of the following classes: antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesics and stimulants.

Typically, where the drug is an antibiotic, it is selected from one of the following compounds: cefmetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

Typically, where the drug is an anticonvulsant, it is selected from one of the following compounds: gabapentin, tiagabine, and vigabatrin.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron methanesulfonate, droperidol, granisetron, hyoscine, lorazepam, metoclopramide, metopimazine, ondansetron, perphenazine, promethazine, prochlorperazine, scopolamine, triethylperazine, trifluoperazine, triflupromazine, trimethobenzamide, tropisetron, domeridone, and palonosetron.

Typically, where the drug is an antihistamine, it is selected from one of the following compounds: azatadine, brompheniramine, chlorpheniramine, clemastine, cyproheptadine, dexmedetomidine, diphenhydramine, doxylamine, hydroxyzine, cetrizine, fexofenadine, loratidine, and promethazine.

Typically, where the drug is an antiparkisonian drug, it is selected one of the following compounds: amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Typically, where the drug is an antipsychotic, it is selected from one of the following compounds: acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, butaclamol, clozapine, melperone, olanzapine, quetiapine, and risperidone.

Typically, where the drug is an anxiolytic, it is selected from one of the following compounds: mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Typically, where the drug is a drug for erectile dysfunction, it is selected from one of the following compounds: cialis (IC351), sildenafil, vardenafil, apomorphine, apomorphine diacetate, phentolamine, and yohimbine.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a drug for the treatment of alcoholism, it is selected from one of the following compounds: naloxone, naltrexone, and disulfuram.

Typically, where the drug is a drug for the treatment of addiction it is buprenorphine.

Typically, where the drug is a muscle relaxant, it is selected from one of the following compounds: baclofen, cyclobenzaprine, orphenadrine, quinine, and tizanidine.

Typically, where the drug is a nonsteroidal anti-inflammatory, it is selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papavereturn, pethidine, pentazocine, phenazocine, remifentanil, sufentanil, and tramadol.

Typically, where the drug is an other analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is a stimulant, it is selected from one of the following compounds: amphetamine, brucine, caffeine, dexfenfluramine, dextroamphetamine, ephedrine, fenfluramine, mazindol, methylphenidate, pemoline, phentermine, and sibutramine.

BRIEF DESCRIPTION OF THE DRAWINGS

Further features and advantages will become apparent from the following description of various examples of the invention, as illustrated in the accompanying drawings in which:

FIG. 29 is a plot of the theoretical size (diameter) of an aerosol as a function of the ratio of the vaporized compound to the volume of the mixing gas.

DETAILED DESCRIPTION

Definitions

Figure 1:
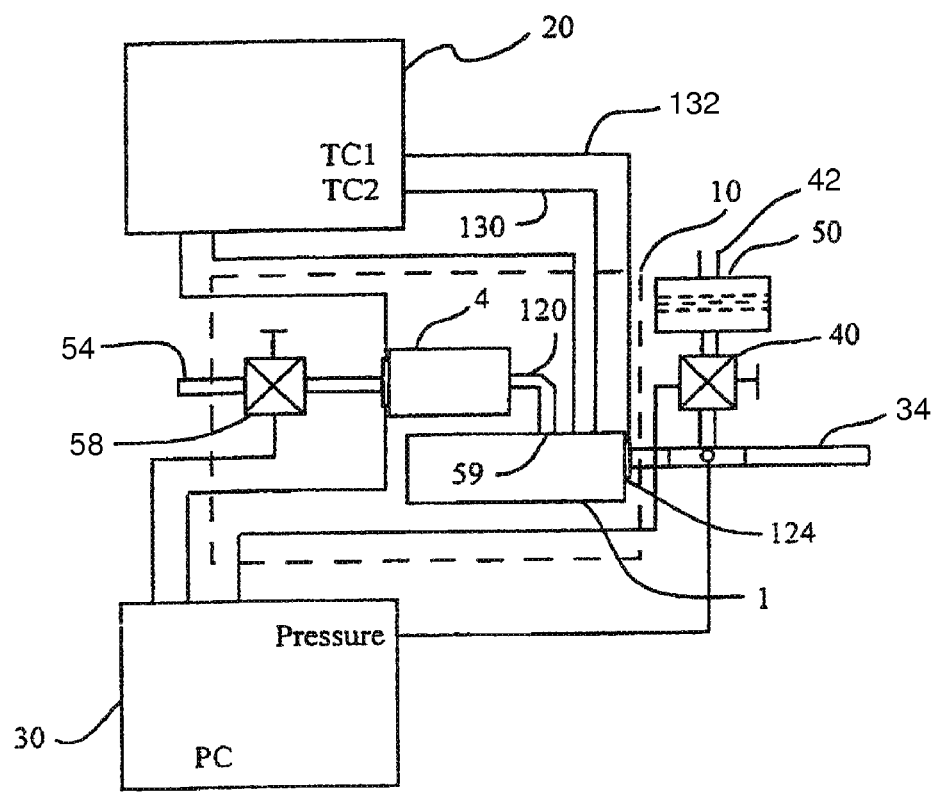
FIG. 1 is a schematic diagram of the overall system for conducting experiments using a laboratory example of a device of the present invention.
Figure 2:
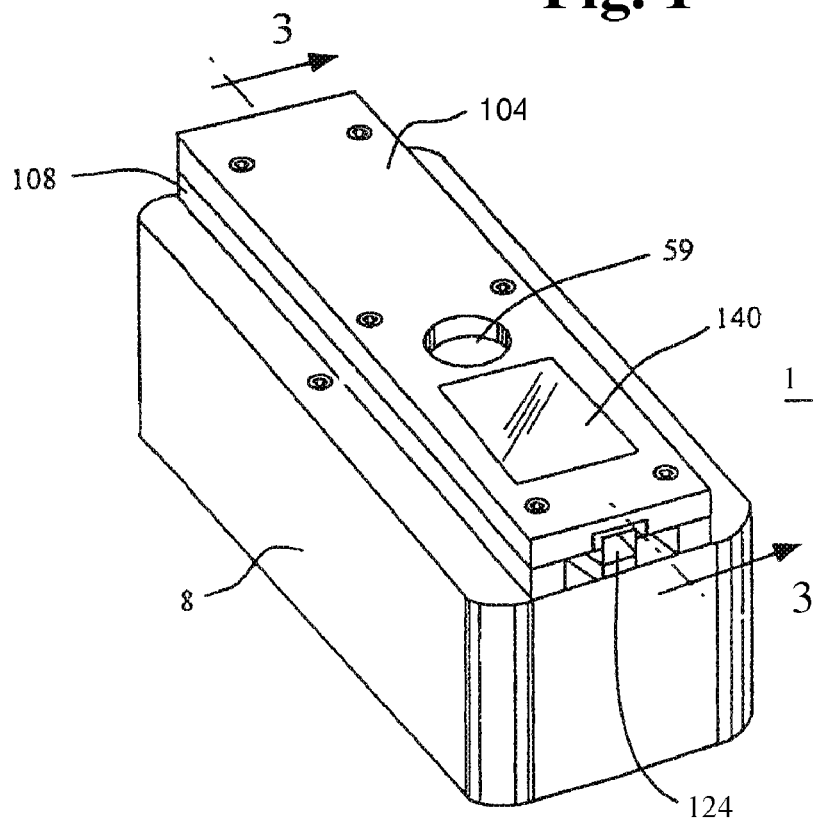
FIG. 2 is a top, right end and front perspective view of the example depicted in FIG. 1.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Decomposition index" refers to a number derived from an assay described in Example 9. The number is determined by substracting the percent purity of the generated aerosol from 1.

"Drug" refers to any chemical compound that is used in the prevention, diagnosis, treatment, or cure of disease, for the relief of pain, or to control or improve any physiological or pathological disorder in humans or animals. Such compounds are oftentimes listed in the Physician's Desk Reference (Medical Economics Company, Inc. at Montvale, N.J., 56$^{th}$ edition, 2002), which is herein incorporated by reference.

Exemplary drugs include the following: cannabanoid extracts from cannabis, THC, ketorolac, fentanyl, morphine, testosterone, ibuprofen, codeine, nicotine, Vitamin A, Vitamin E acetate, Vitamin E, nitroglycerin, pilocarpine, mescaline, testosterone enanthate, menthol, phencaramkde, methsuximide, eptastigmine, promethazine, procaine, retinol, lidocaine, trimeprazine, isosorbide dinitrate, timolol, methyprylon, etamiphyllin, propoxyphene, salmetrol, vitamin E succinate, methadone, oxprenolol, isoproterenol bitartrate, etaqualone, Vitamin D3, ethambutol, ritodrine, omoconazole, cocaine, lomustine, ketamine, ketoprofen, cilazaprol, propranolol, sufentanil, metaproterenol, prentoxapylline, testosterone proprionate, valproic acid, acebutolol, terbutaline, diazepam, topiramate, pentobarbital, alfentanil HCl, papaverine, nicergoline, fluconazole, zafirlukast, testosterone acetate, droperidol, atenolol, metoclopramide, enalapril, albuterol, ketotifen, isoproterenol, amiodarone HCl, zileuton, midazolam, oxycodone, cilostazol, propofol, nabilone, gabapentin, famotidine, lorezepam, naltrexone, acetaminophen, sumatriptan, bitolterol, nifedipine, Phenobarbital, phentolamine, 13-cis retinoic acid, droprenilamin HCl, amlodipine, caffeine, zopiclone, tramadol HCl, pirbuterol naloxone, meperidine HCl, trimethobenzamide, nalmefene, scopolamine, sildenafil, carbamazepine, procaterol HCl, methysergide, glutathione, olanzapine, zolpidem, levorphanol, buspirone and mixtures thereof.

Typically, the drug of the composition is of one of the following classes: antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesics, cannabanoids, and stimulants.

Typically, where the drug is an antibiotic, it is selected from one of the following compounds: cefmetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

Typically, where the drug is an anticonvulsant, it is selected from one of the following compounds: gabapentin, tiagabine, and vigabatrin.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron methanesulfonate, dronabinol, droperidol, granisetron, hyoscine, lorazepam, metoclopramide, metopimazine, ondansetron, perphenazine, promethazine, prochlorperazine, scopolamine, triethylperazine, trifluoperazine, triflupromazine, trimethobenzamide, tropisetron, domeridone, and palonosetron.

Typically, where the drug is an antihistamine, it is selected from one of the following compounds: azatadine, brompheniramine, chlorpheniramine, clemastine, cyproheptadine, dexmedetomidine, diphenhydramine, doxylamine, hydroxyzine, cetrizine, fexofenadine, loratidine, and promethazine.

Typically, where the drug is an antiparkisonian drug, it is selected one of the following compounds: amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Typically, where the drug is an antipsychotic, it is selected from one of the following compounds: acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, butaclamol, clozapine, melperone, olanzapine, quetiapine, and risperidone.

Typically, where the drug is an anxiolytic, it is selected from one of the following compounds: mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Typically, where the drug is a drug for erectile dysfunction, it is selected from one of the following compounds: cialis (IC351), sildenafil, vardenafil, apomorphine, apomorphine diacetate, phentolamine, and yohimbine.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a drug for the treatment of alcoholism, it is selected from one of the following compounds: naloxone, naltrexone, and disulfuram.

Typically, where the drug is a drug for the treatment of addiction it is buprenorphine.

Typically, where the drug is a muscle relaxant, it is selected from one of the following compounds: baclofen, cyclobenzaprine, orphenadrine, quinine, and tizanidine.

Typically, where the drug is a nonsteroidal anti-inflammatory, it is selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papavereturn, pethidine, pentazocine, phenazocine, remifentanil, sufentanil, and tramadol.

Typically, where the drug is an other analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is a cannabanoid, it is tetrahydrocannabinol (e.g., delta-8 or delta-9).

Typically, where the drug is a stimulant, it is selected from one of the following compounds: amphetamine, brucine, caffeine, dexfenfluramine, dextroamphetamine, ephedrine, fenfluramine, mazindol, methyphenidate, pemoline, phentermine, and sibutramine.

"Drug degradation product" refers to a compound resulting from a chemical modification of a drug. The modification, for example, can be the result of a thermally or photochemically induced reaction. Such reactions include, without limitation, oxidation and hydrolysis.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Stable aerosol" refers to an aerosol where the MMAD of its constituent particles does not vary by more than 50% over a set period of time. For example, an aerosol with an MMAD of 100 nm is stable over 1 s, if at a time 1 second later it has an MMAD between 50 nm and 150 nm. Preferably, the MMAD does not vary by more than 25% over a set period of time. More preferably, the MMAD does not vary by more than 20%, 15%, 10% or 5% over time.

Aerosolization Device

Example 1 is described in terms of an in vivo dog experiment. The example, however, is easily modified to suit human inhalation primarily through increasing airflow through it.

Referring to FIGS. 1-8, a first example (1) of an aerosolization device of the present invention will be described. The device 1 as shown in FIG. 1 is operably connected to flow meter 4 (e.g., a TSI 4100 flow meter). The readings from flow meter 4 are fed to the electronics within chassis 8 shown in FIG. 2. Flow meter 4 is shown in FIG. 1 within a dotted line to indicate housing 10. Device controller 20 includes Chembook model # N30W laptop computer having actuator switch 22 (FIG. 3) and National Instruments I/O Board (model #SC2345) (not shown) that interfaces with computer 20 to control device 1 and to control the recording of all data collected during the experiments. A software program to carry out these functions was developed using National Instruments' Labview software program.

Connection between device 1 and the I/O board is accomplished with a cable (e.g., DB25, not shown). A standard power supply (e.g., Condor F15-15-A+ not shown) delivers power to device 1. Inhalation controller 30 is used to control the rate and volume of inhalation through device 1 into an anesthetized dog through an endotracheal tube 34. Controller 30 has a programmable breath hold delay, at the end of which, exhaust valve 40 in exhaust line 42 opens and the dog is allowed to exhale. Filter 50 in line 42 measures the amount of exhaust and its composition to monitor any exhaled drug. The source air through inlet line 54, inlet valve 58, flow meter 4 and inlet orifice 59 is from a compressed air cylinder (not shown).

Now referring to FIGS. 3-5 and 7, a dose of compound 60 is deposited onto thin, stainless steel foil 64 so that the thickness of compound 60 is less than 10 microns. In most cases, compound 60 is deposited by making a solution of the compound with an organic solvent. This mixture is then applied to the foil substrate with an automated pump system. As shown, the size of the entire foil 64 (e.g., alloy of 302 or 304 with 0.004 in. thickness) is 0.7 by 2.9 inches and the area in which compound 60 is deposited is 0.35 by 1.6 inches. Other foil materials can be used but stainless steel has an advantage over other materials like aluminum in that it has a much lower thermal conductivity value, while not appreciably increasing the thermal mass. A low thermal conductivity is helpful because the heat generated in foil 64 should stay in the area of interest (i.e., the heating/vaporization zone 70). Foil 64 should have a constant cross section, because otherwise the electrical currents induced by the heater will not be uniform. Foil 64 is held in frame 68, made so that the trailing edge of foil 64 has no lip on movable slide 78 and so compound 60, once mixed with the air, is free in a downstream direction as indicated by arrow 127 of FIG. 3. Frame 68 is typically made of a non-conductive material to withstand moderate heat (e.g., 200° C.) and to be non-chemically reactive with the compound (e.g., DELRIN AF®, a copolymer of acetal and TEFLON®).

Figure 5:
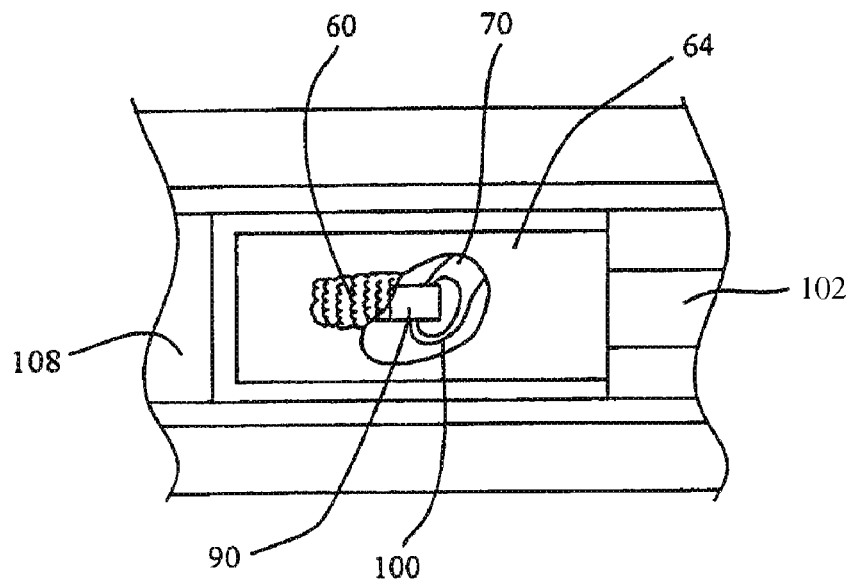
FIG. 5 is a partial cross-sectional and partial schematic top view of the example shown in FIG. 2.
Figure 7:
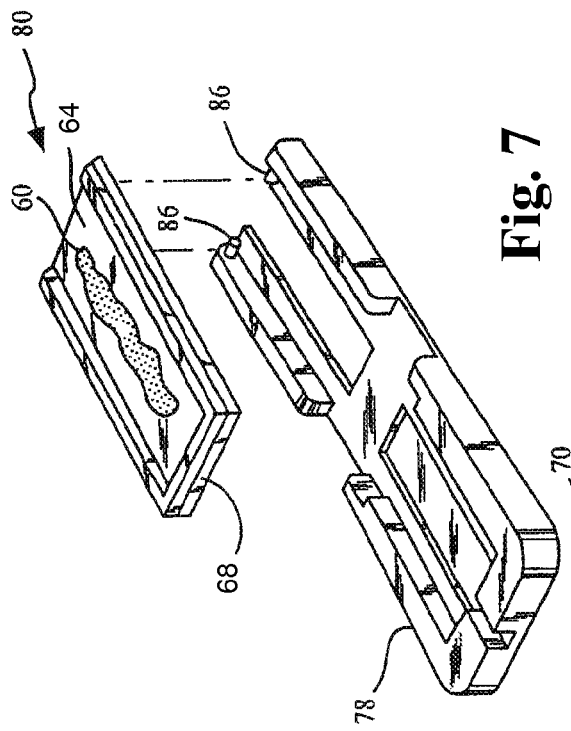
FIG. 7 is a top, left end and front perspective views of the removable sub-assembly containing the compound and a movable slide of the example shown in FIG. 2 showing the sub-assembly being mounted within the slide.

Sub-assembly 80, shown in FIG. 7, consists of frame 68 having compound (60) coated foil 64 mounted therein. Sub-assembly 80 is secured within movable slide 78 by setting each of the downstream, tapered ends of frame 68 to abut against small rods 86 protruding from each downstream end of slide 78, as shown in FIG. 7. Slide 78 is driven by stepper motor 88, shown in FIG. 3, that moves sub-assembly 80 containing compound 60 along the longitudinal axis of example 1. This, in turn, moves stainless steel foil 64 through an alternating magnetic field. (It is preferable for the magnetic field to be confined within heating/vaporization zone 70, shown in FIG. 5, as in this laboratory example.) Ferrite toroid 90 is used to direct the magnetic field and is placed below foil 64 (e.g., approximately 0.05 inches below). As shown in FIG. 5, heated area 70 is approximately 0.15 by 0.4 inches, with the smaller dimension along the direction of travel from left to right (i.e., from the upstream to the downstream ends of device 1) and the large dimension across the direction of travel (i.e., the width of device 1).

Foil 64 functions as both a substrate for the drug to be delivered to the subject and the heating element for the vaporization of the drug. Heating element 64 is heated primarily by eddy currents induced by an alternating magnetic field. The alternating magnetic field is produced in ferrite toroid 90 (e.g., from Fair-Rite Company) with slit 94 (e.g., 0.10 in. wide), which was wrapped with coil 98 of copper magnet wire. When an alternating current is passed through coil 98, an alternating magnetic field is produced in ferrite toroid 90. A magnetic field fills the gap formed by slit 94 and magnetic field fringe lines 100, shown in FIGS. 5 and 6, extend out from toroid 90. The magnetic field line fringe lines 100 intersect heating element 64. When using a ferrite core, the alternating frequency of the field is limited to below 1 MHz. In this device, a frequency between 100 and 300 kHz is typically used.

The location and geometry of the eddy currents determine where foil 64 will be heated. Since magnetic field fringe lines 100 pass through foil 64 twice, once leaving ferrite toroid 90 and once returning, two rings of current are produced, and in opposite directions. One of the rings is formed around magnetic field lines 100 that leave toroid 90 and the other ring forms around magnetic field lines 100 that return toroid 90. The rings of current overlap directly over the center of slit 94. Since they were in opposite directions, they sum together. The greatest heating effect is therefore produced over the center of slit 94.

Figure 3:
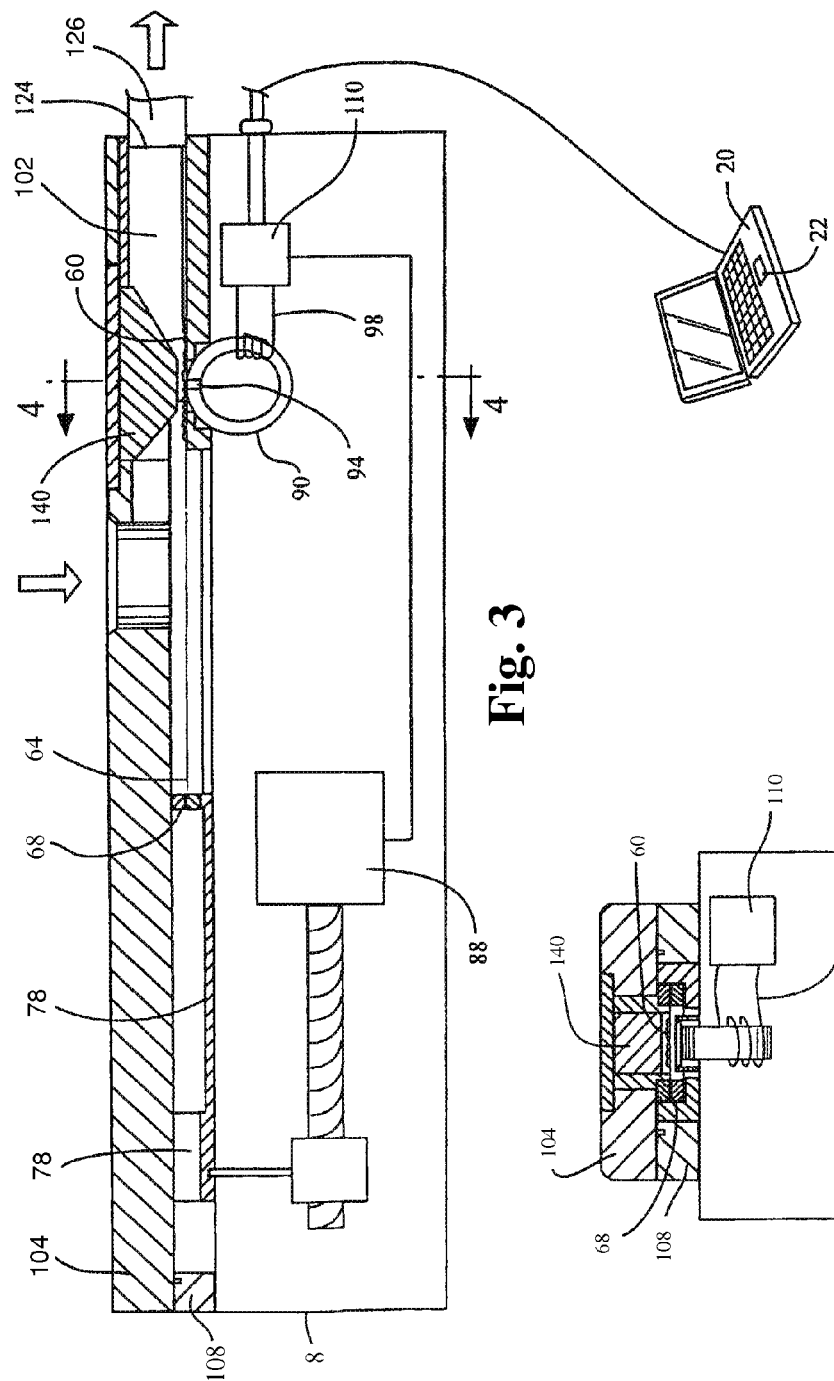
FIG. 3 is a partial cross-sectional and partial schematic side view of the example shown in FIG. 2.
Figure 4:
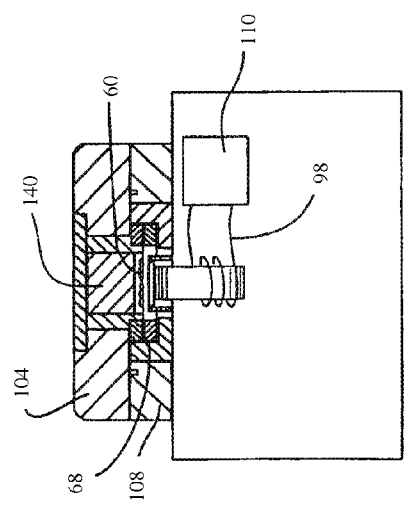
FIG. 4 is a partial cross-sectional and partial schematic end view of the example shown in FIG. 2.

Slide 78 and its contents are housed in airway 102 made up of upper airway section 104 and lower airway section 108 shown in FIG. 3. Upper airway section 104 is removable and allows the insertion of movable slide 78, sub-assembly 80 and foil 64. Lower airway section 108 is mounted on top of chassis 8 that houses the electronics (not shown), magnetic field generator 110, stepper motor 88 and position sensors (not shown). Referring again to FIG. 1, mounted in upper airway section 104 is upstream passage 120 and inlet orifice 59 that couples upper airway section 104 to flow meter 4. The readings from the flow meter 4 are fed to the electronics housed in chassis 8. Additionally, at the downstream end of airway passage 102, outlet 124 is connected to mouthpiece 126. During administration of compound 60 to the dog, when joined to the system, air is forced through inlet line 54, flow meter 4, airway 102, and outlet 124 into the dog.

Additionally, a pyrometer at the end of TC2 line 130 is located within airway 102 and is used to measure the temperature of foil 64. Because of the specific geometry of the example shown in FIGS. 1-7, the temperature reading of foil 64 is taken after heating zone 70. Calibration of the thermal decay between heating zone 70 and the measurement area is required. Temperature data is collected and used for quality control and verification and not to control any heating parameters. A second temperature sensor is located at the end of TC1 line 132 in outlet 124 and is used to monitor the temperature of the air delivered to the dog.

In a preferred example of the experimental device, removable block 140, mounted on upper airway section 104, restricts a cross-sectional area of airway 102 and provides a specific mixing geometry therein. In this preferred example, airway 140 lowers the roof of upper airway section 104 (e.g., to within 0.04 inch of) with respect to foil 64. Additionally, block 140 contains baffles (e.g., 31 steel rods 0.04 in. in diameter, not shown). The rods are oriented perpendicular to the foil and extend from the top of upper airway section 104 to within a small distance of the foil (e.g., 0.004 in.). The rods are placed in a staggered pattern and have sharp, squared off ends, which cause turbulence as air passes around them. This turbulence assures complete mixing of vaporized compounds with air passing through the device.

A second example (150) of an aerosolization device of the present invention, in which the cross-sectional area is also restricted along the gas/vapor mixing area, will be described in reference to FIG. 9. In this example, venturi tube 152 within housing 10 having inlet 154, outlet 156 includes a throat 158 between inlet 154 and outlet 156, which is used to restrict the gas flow through venturi tube 152. Additionally, a controller 160 is designed to control the flow of air passing through a valve 164 based on readings from the thermocouple 168 of the temperature of the air, which can be controlled by heater 166.

Block 140 is located directly over heating zone 70 and creates a heating/vaporization/mixing zone. Prior to commencing aerosol generation, slide 78 is in the downstream position. Slide 78, with its contents, is then drawn upstream into this heating/vaporization/mixing zone 70 as energy is applied to foil 64 through the inductive heater system described in detail below.

Figure 6:
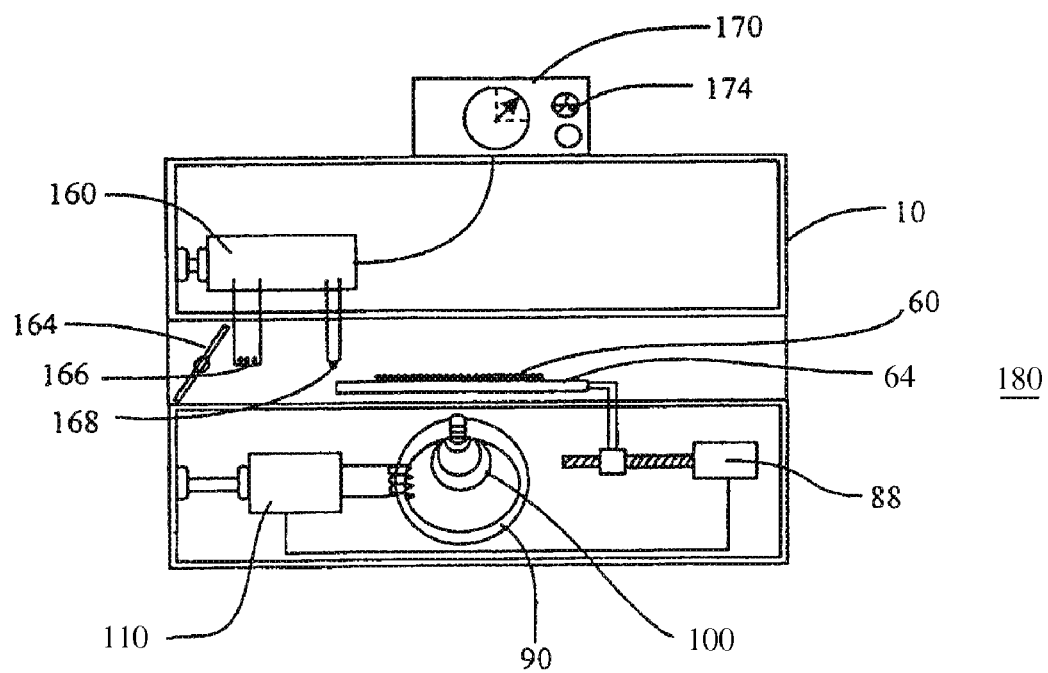
FIG. 6 is a schematic cross-sectional side view of an alternate example of the device of the present invention using an annunciating device.

The device of the present invention is optionally equipped with an annunciating device. One of the many functions for the annunciating device is to alert the operator of the device that a compound is not being vaporized or is being improperly vaporized. The annunciating device can also be used to alert the operator that the gas flow rate is outside a desired range. FIG. 6 is a schematic diagram illustrating a third example of a hand held aerosolization device 180 of the present invention. As shown, device 180 includes many of the components of device 150, discussed above, and additionally includes an annunciating device 170. During the use of device 180 in which the patient's inhalation rate controls the airflow rate, a signal from annunciating device 170 would alert the patient to adjust the inhalation rate to the desired range. In this case, controller 160 would be connected to annunciating device 170 to send the necessary signal that the flow rate was not within the desired range.

Figure 8:
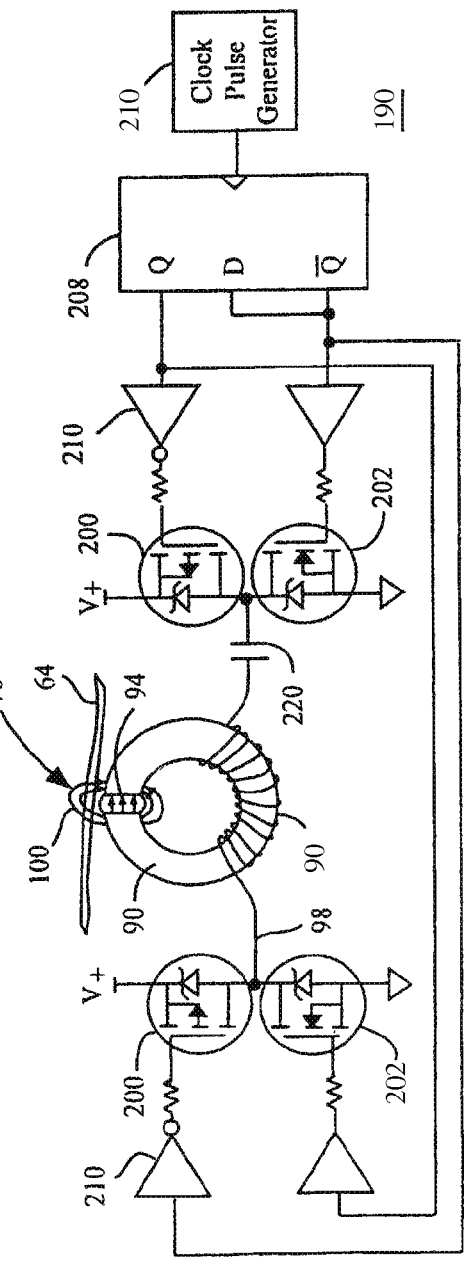
FIG. 8 is a schematic view of the heating element of the example shown in FIG. 2 showing the electric drive circuit.

The induction drive circuit 190 shown in FIG. 8 is used to drive the induction-heating element of device 1. The purpose of circuit 190 is to produce an alternating current in drive coil 98 wrapped around ferrite core 90. Circuit 190 consists of two P-channel transistors 200 and two N-channel MOSFET transistors 202 arranged in a bridge configuration. MOSFET transistors 200 and 202 connected to clock pulse generator 219 are turned on and off in pairs by D-type flip-flop 208 through MOSFET transistor drive circuit 210. D-type flip-flop 208 is wired to cause the Q output of the flip-flop to alternately change state with the rising edge of the clock generation signal. One pair of MOSFET transistors 200 is connected to the Q output on D-type flip-flop 208 and the other pair, 202, is connected to the Q-not output of flip-flop 208. When Q is high (5 Volts), a low impedance connection is made between the D.C. power supply (not shown) and the series combination of drive coil 98 and the capacitor through the pair of MOSFET transistors 200 controlled by the Q output. When D-type flip-flop 208 changes state and Q-not is high, the low impedance connection from the power supply to the series combination drive coil 98 and capacitor 220 is reversed. Since flip-flop 208 changes state on the rising edge of the clock generation signal, two flip-flop changes are required for one complete drive cycle of the induction-heating element. The clock generation signal is typically set at twice the resonant frequency of the series combination of drive coil 90 and capacitor 220. The clock signal frequency can be manually or automatically set.

A second example (150) of an aerosolization device of the present invention, in which the cross-sectional area is also restricted along the gas/vapor mixing area, will be described in reference to FIG. 9. In this example, venturi tube 152 within housing 10 having inlet 154, outlet 156 and throat 158 between inlet 154 and outlet 156 is used to restrict the gas flow through venturi tube 152. Controller 160 is designed to control the flow of air passing through valve 164 based on readings from the thermocouple 168 of the temperature of the air as a result of heater 166.

Figure 10:
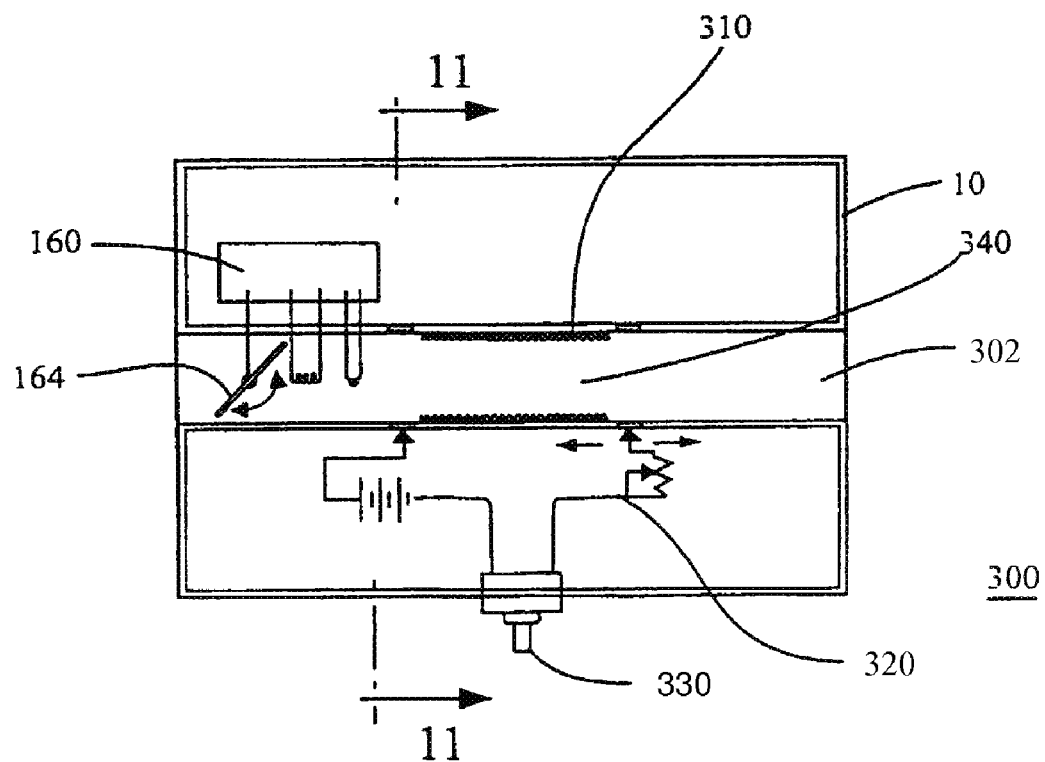
FIG. 10 is a schematic side view of a fourth example of the present invention using a thin-walled tube coated with the compound.
Figure 11:
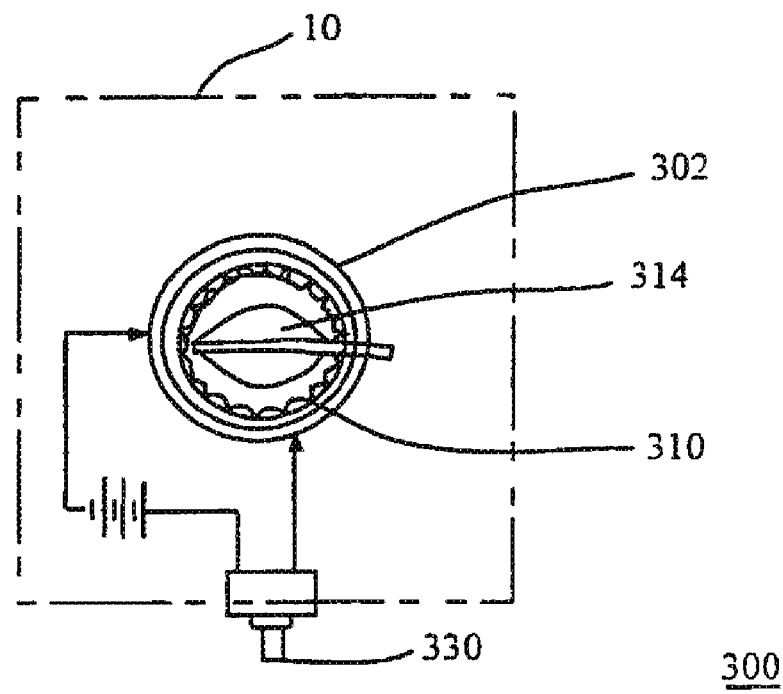
FIG. 11 is a schematic side end view of the example shown in FIG. 10.

A fourth example (300) of an aerosolization device of the present invention will be described in reference to FIGS. 10 and 11. A gas stream is passed into thin walled tube 302 having a coating (310) of compound 60 on its inside. The flow rate of the gas stream is controlled by valve 314. The device of example 300, as with others, allows for rapid heat-up using a resistive heating system (320) while controlling the flow direction of vaporized compound. After activating heating system 320 with actuator 330, current is passed along tube 302 in the heating/vaporization zone 340 as the carrier gas (e.g., air, $N_2$ and the like) is passed through tube 302 and mixes with the resulting vapor.

Figure 12:
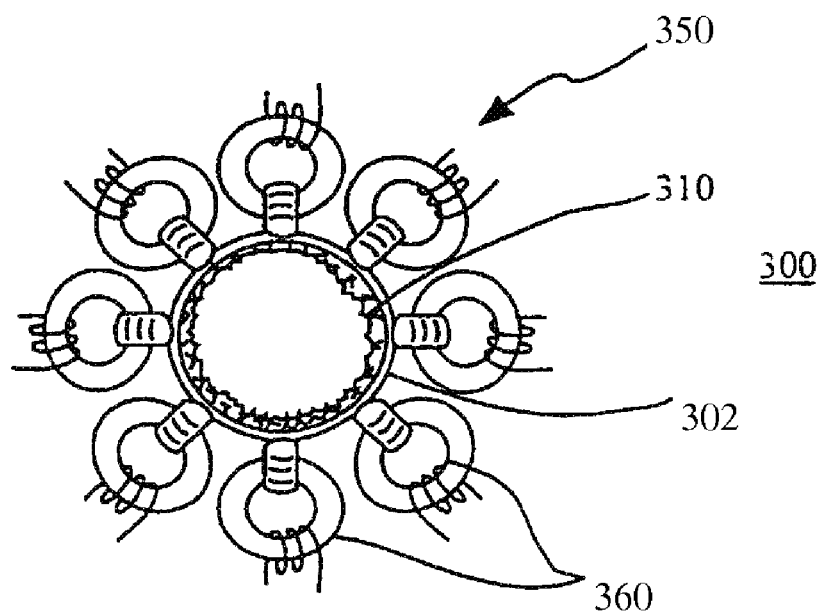
FIG. 12 is a schematic side end view of the example shown in FIG. 10 showing an inductive heating system generating an alternating magnetic field.

FIG. 12 shows an alternative heating system to resistive heating system 320 used in connection with the fourth example. In this case, inductive heating system 350 consists of a plurality of ferrites 360 for conducting the magnetic flux to vaporize compound 310.

Figure 13:
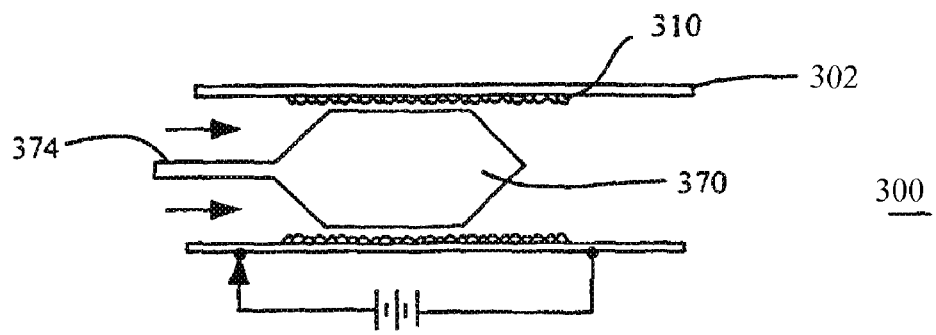
FIG. 13 is a schematic side view of an alternate example of that shown in FIG. 10 using a flow restrictor within the thin-walled tube.

FIG. 13 shows a variation on the fourth example in which flow restrictor 370 is mounted within thin-walled tube 302 by means of support 374 within a housing (not shown) to increase the flow of mixing gas across the surface of compound 310.

Figure 14:
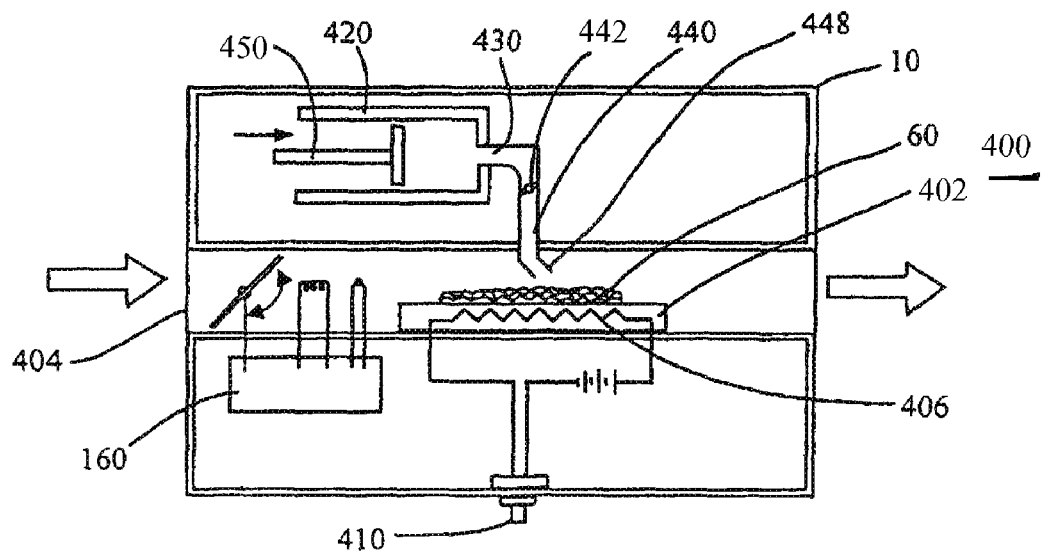
FIG. 14 is a schematic side view of a fifth example of the present invention using an expandable container for the compound.

A fifth example 400 of an aerosolization device of the present invention will be described in reference to FIG. 14. For this example, compound 60 is placed within expandable container 402 (e.g., a foil pouch) and is heated by resistance heater 406, which is activated by actuator 410 as shown in FIG. 14. The vaporized compound generated is forced into container 420 through outlet passage 440 and mixed with the gas flowing through tube 404. Additional steps are taken, when necessary, to preclude or retard decomposition of compound 60. One such step is the removal or reduction of oxygen around 60 during the heat up period. This can be accomplished, for example, by sealing the small container housing in an inert atmosphere.

Figure 15:
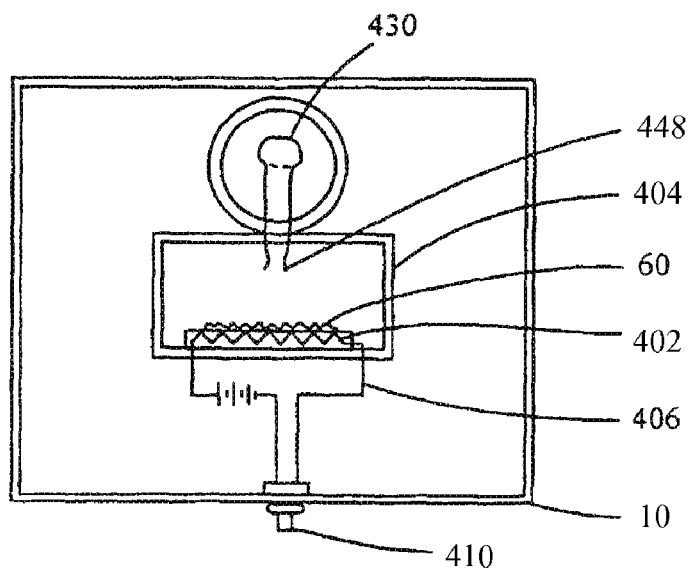
FIG. 15 is a schematic side view of a sixth example of the present invention using a container for the compound in an inert atmosphere.

A sixth example 500 of an aerosolization device of the present invention will be described in reference to FIG. 15. Compound 60 is placed in an inert atmosphere or under a vacuum in container 502 within housing 10 and is heated by resistance heater 504 upon being activated by actuator 508 as shown in FIG. 15. Once compound 60 has become vaporized it can then be ejected through outlet passage 510 into the air stream passing through tube 520.

Figure 16:
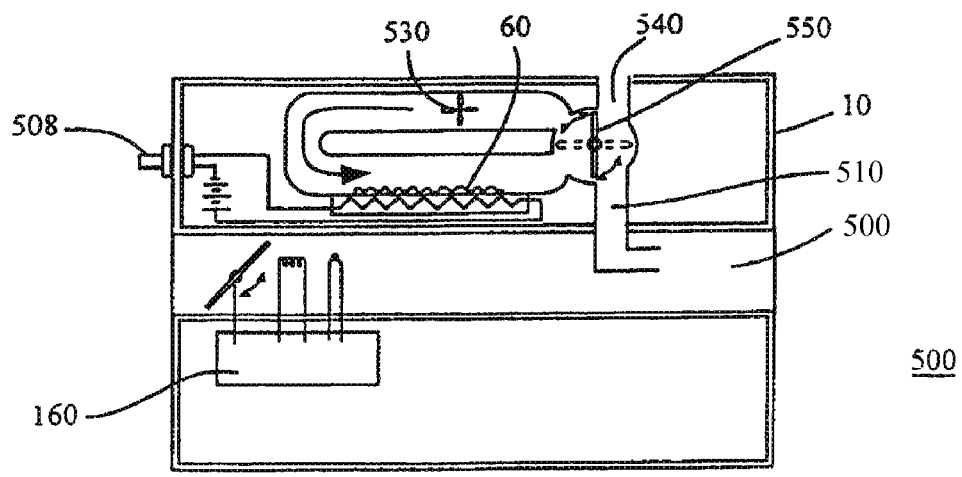
FIG. 16 is a schematic side view of the example shown in FIG. 15 using a re-circulation of the inert atmosphere over the compound's surface.

FIG. 16 shows a variation of device 500 in which fan 530 recirculates the inert atmosphere over the surface of compound 60. The inert gas from a compressed gas cylinder (not shown) enters through inlet 540 and one-way valve 550 and exits through outlet passage 510 into tube 502.

A seventh example (600) of an aerosolization device of the present invention will be described in reference to FIG. 17. A compound (not shown), such as compound 60 discussed above, is deposited onto a substrate in the form of discrete particles 602 (e.g., aluminum oxide (alumina), silica, coated silica, carbon, graphite, diatomaceous earth, and other packing materials commonly used in gas chromatography). The coated particles are placed within first tube 604, sandwiched between filters 606 and 608, and heated by resistance heater 610, which is activated by actuator 620. The resulting vapor from tube 604 is combined with the air or other gas passing through second tube 625.

Figure 18:
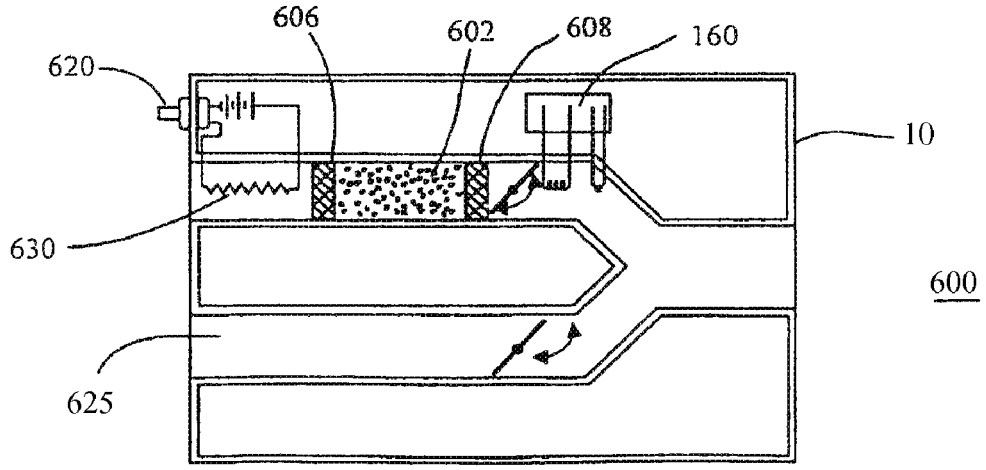
FIG. 18 is a schematic side view of the example shown in FIG. 17 using a heating system to heat the gas passing over the coated particles.

FIG. 18 shows a variation of device 600 in which resistance heater 630 heats the air prior to passing through first tube 604 and over discrete particles 602.

An eighth example 700 of an aerosolization device of the present invention will be described in reference to FIG. 19. Compound 60 is deposited into chamber 710 and is heated by resistance heater 715, which is activated by actuator 720. Upon heating, some of compound 60 is vaporized and ejected from chamber 710 by passing an inert gas entering housing 10 through inert gas inlet 725 and valve 728 across the surface of the compound. The mixture of inert gas and vaporized compound passes through passage 730 and is then mixed with a gas passing through tube 735.

A ninth example 800 of an aerosolization device of the present invention will be described in reference to FIG. 20. Thermally conductive substrate 802 is heated by resistance heater 810 at the upstream end of tube 820, and the thermal energy is allowed to travel along substrate 802. This produces, when observed in a particular location, a heat up rate that is determined from the characteristics of the thermally conductive substrate. By varying the material and its cross sectional area, it was possible to control the rate of heat up. The resistive heater is embedded in substrate 802 at one end. However, it could be embedded into both ends, or in a variety of positions along the substrate and still allow the temperature gradient to move along the carrier and/or substrate.

A tenth example 900 of an aerosolization device of the present invention will be described in reference to FIGS. 21 and 22. Air is channeled through a fine mesh metal screen 902 on which drug is deposited. Screen 902 is positioned across airway passage 910 (e.g., constructed from 18 mm glass tubing). The two sides of the screen are electrically connected to charged capacitor 920 through silicon-controlled rectifier (SCR) 922 to make a circuit. The charge of the capacitor is calculated and set at a value such that, when actuator 930 closes SCR 922, the energy from capacitor 920 is converted to a desired temperature rise in screen 902.

General Considerations

The device of the present invention utilizes a flow of gas (e.g., air) across the surface of a compound (60) to sweep away vaporized molecules. This process drives vaporization as opposed to condensation and therefore enables aerosol formation at relatively moderate temperatures. Nicotine (1 mg, bp 247° C./745 mm), for example, vaporized in less than 2 s at about 130° C. in a device of the present invention. Similarly, fentanyl (bp>300° C./760 mm) was vaporized around 190° C. in quantities up to 2 mg.

Purity of an aerosol produced using a device of the present invention is enhanced by limiting the time at which a compound (60) is exposed to elevated temperatures. This is accomplished by rapidly heating a thin film of the compound to vaporize it. The vapors are then immediately cooled upon entry into a carrier gas stream.

Typically, compound 60 is subjected to a temperature rise of at least 1,000° C./second. In certain cases, the compound is subjected to a temperature rise of at least 2,000° C./second, 5,000° C./second, 7,500° C. or 10,000° C./second. A rapid temperature rise within the compound is facilitated when it is coated as a thin film (e.g., less than 10μ, 5μ, 4μ, 3μ, 2μ, or 1μ in thickness). The compound is oftentimes coated as a film between 10μ and 10 nm, 5μ and 10 nm, 4μ and 10 nm, 3μ and 10 nm, 2μ and 10 nm, or even 1μ to 10 nm in thickness.

Rapid temperature rises and thin coatings ensure that compounds are substantially vaporized in a short time. Typically, greater than 0.1 mg, 0.25 mg, 0.5 mg, 0.75 mg or 1 mg of a compound is vaporized in less than 100 milliseconds from the start of heating. Oftentimes, the same amount of compound is vaporized in less than 75 milliseconds, 50 milliseconds, 25 milliseconds, or 10 milliseconds from the start of heating.

Examples of compounds that have benefited from rapid heating in a device of the present invention include lipophilic substance #87 and fentanyl. Lipophilic substance #87 decomposed by more than 90% when heated at 425° C. for 5 minutes, but only 20% when the temperature was lowered to 350° C. Decomposition of the substance was further lowered to about 12% when the heating time was decreased to 30 seconds and to less than 2% at 10-50 milliseconds. A fentanyl sample decomposed entirely when heated to 200° C. for 30 seconds, and only 15-30% decomposed when heated for 10 milliseconds. Vaporizing fentanyl in device 1 led to less than 0.1% decomposition.

Figure 23:
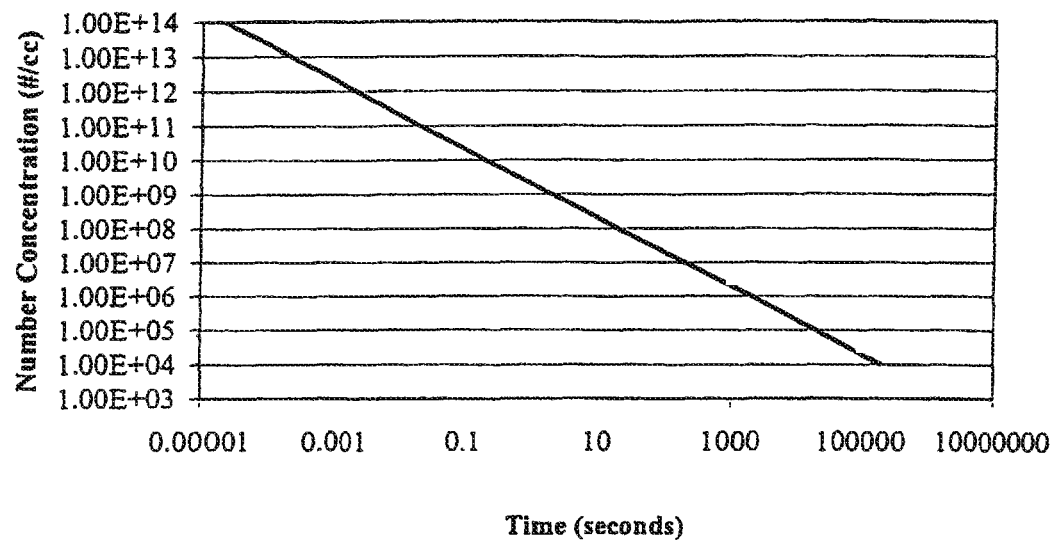
FIG. 23 is a plot of the rate of aggregation of smaller particles into larger ones.

FIG. 23 is a plot of theoretical data calculated from a mathematical model. See "Aerosol Technology" W. C. Hinds, second edition 1999, Wiley, New York. It shows the time in seconds it takes for the number concentration of an aerosol to aggregate to half of its original value as a function of the particle concentration. For example, a 1.0 mg vaporized dose of a compound with a molecular weight of 200 that is mixed into 1 liter of aire will have approximately $3 \times 10^{18}$ molecules (particles) in the liter. This results in a number concentration of $3 \times 10^{15}$/cc. Extrapolating from FIG. 23, one can see that it takes less than 10 milliseconds for the number of particles to halve in this example. Therefore, to insure uniform mixing of a vaporized compound, the mixing must occur in a very short time. FIG. 23 also shows that when the number concentration of the mixture reaches approximately $10^9$ particles/cc, the particle size is "stable" for the purpose of drug delivery by inhalation.

Figure 24:
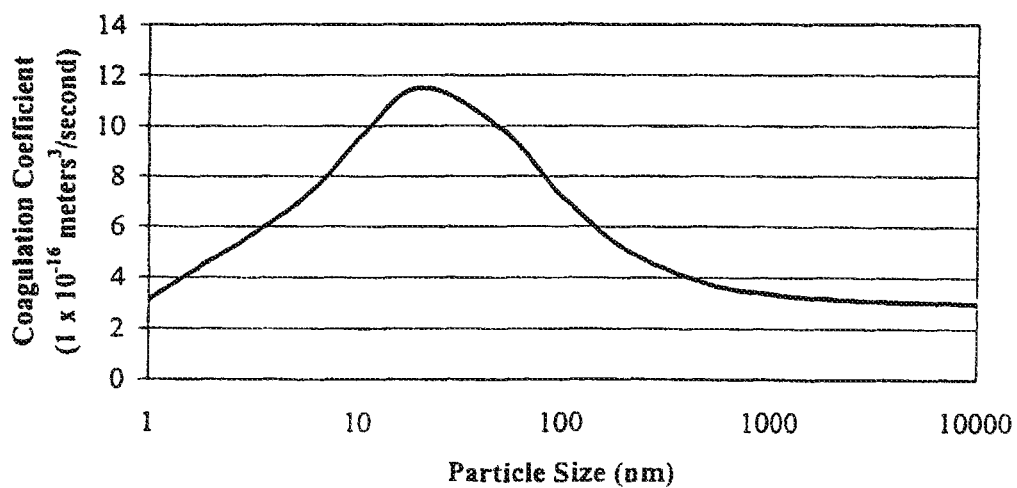
FIG. 24 is a plot of the coagulation coefficient (K) versus particle size of the compound.
Figure 25:
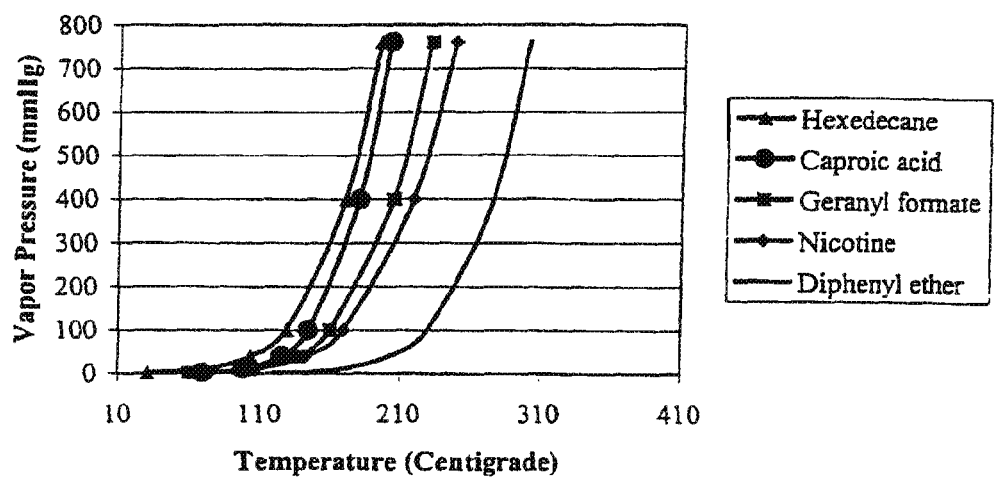
FIG. 25 is a plot of vapor pressure of various compounds, e.g., diphenyl ether, hexadecane, geranyl formate and caproic acid, versus temperature.

FIG. 23 is for an aerosol having a Coagulation Coefficient (K) of $5 \times 10^{-16}$ meters$^3$/second. This K value corresponds to a particle size of 200 nm. As the particle size changes, so can its K value. Table 1 below gives the K values for various particle sizes. As K increases, the time required for the aerosol to aggregate from a particular particle size to a larger particle size is reduced. As can be seen from Table 1 and FIG. 24, when the particle is in the 10 nm to 100 nm range, the effect of a changing K value tends to accelerate the coagulation process towards 100 nm in size.

TABLE 1

| Particle size (diameter in nm) | Coagulation Coefficient (x $e^{-15}$ meters$^3$/second) |
|---|---|
| 1 | 3.11 |
| 5 | 6.93 |
| 10 | 9.48 |
| 20 | 11.50 |
| 50 | 9.92 |
| 100 | 7.17 |
| 200 | 5.09 |
| 500 | 3.76 |
| 1000 | 3.35 |
| 2000 | 3.15 |
| 5000 | 3.04 |
| 10000 | 3.00 |

In creating an aerosol of a particular particle size, the ratio of mass of vaporized compound to the volume of the mixing gas is the controlling condition. By changing this ratio, the particle size can be manipulated (see FIG. 29). However, not all compounds and not all gases, with the same ratio will result in the same particle size distribution (PSD). Other factors must be known to be able to accurately predict the resultant particle size. A compound's density, polarity, and temperature are examples of some of these factors. Additionally, whether the compound is hydrophilic or hydrophobic will affect the eventual particle size, because this factor affects an aerosol's tendency to grow by taking on water from the surrounding environment.

In order to simplify the approach used to predict the resulting particle size, the following assumptions were made:

1. The compound is non polar (or has a weak polarity).
2. The compound is hydrophobic or hydrophilic with a mixing gas that is dry.
3. The resultant aerosol is at or close to standard temperature and pressure.
4. The coagulation coefficient is constant over the particle size range and therefore the number concentration that predicts the stability of the particle size is constant.

Consequently, the following variables are taken into consideration in predicting the resulting particle size:

1. The amount (in grams) of compound vaporized.
2. The volume of gas (in cc's) that the vaporized compound is mixed into.
3. The "stable" number concentration in number of particles/cc.
4. The geometric standard deviation (GSD) of the aerosol.

Where the GSD is 1, all of the particle sizes are the same size and therefore the calculation of particle size becomes a matter of dividing a compound's mass into the number of particles given by the number concentration and from there calculating the particle size diameter using the density of the compound. The problem becomes different, though, if the GSD is other than 1. As an aerosol changes from a GSD of 1 to a GSD of 1.35, the mass median diameter (MMD) will increase. MMD is the point of equilibrium where an equal mass of material exists in smaller diameter particles as exists in larger diameter particles. Since total mass is not changing as the GSD changes, and since there are large and small particles, the MMD must become larger as the GSD increases because the mass of a particle goes up as the cube of its diameter. Therefore larger particles, in effect, carry more weight and the MMD becomes larger to "balance" out the masses.

To determine the effect of a changing GSD, one can start with the formula for the mass per unit volume of an aerosol given a known MMD, GSD, density, and number concentration. The formula is from Finlay's "*The Mechanics of Inhaled Pharmaceutical Aerosols*" (2001, Academic press). Formula 2.39 states that the mass per unit volume of an aerosol is:

$$M = (\rho N \pi/6)(MMD)^3 \exp[-9/2(\ln \sigma_g)^2]$$

Where:
$\rho$=density in gm/cc
N=Number concentration in particles/cc
MMD=mass median diameter (in cm)
$\sigma_g$=the GSD
M=the mass per unit volume of the aerosol in gms/cc If the change in the MMD is considered as an aerosol changes from one GSD to another, while the density, number concentration, and the mass remain unchanged the following equality can be set up:

$$pN\pi/6(MMD_1)^3 \exp[-9/2(\ln \sigma_{g1})^2] = pN\pi/6(MMD_2)^3 \exp[-9/2(\ln \sigma_{g2})^2]$$

simplifying:

---

$(MMD_1)^3 \exp[-9/2(\ln\sigma_{g1})^2] = (MMD_2)^3 \exp[-9/2(\ln\sigma_{g2})^2]$ Or $(MMD_1)^3/(MMD_2)^3 = \exp[-9/2(\ln\sigma_{g2})^2]/\exp[-9/2(\ln\sigma_{g1})^2]$ If one sets the GSD of case 1 to 1.0 then:

$\exp[-9/2(\ln\sigma_{g1})^2] = 1$

And therefore:

$(MMD_1/MMD_2)^3 = \exp[-9/2(\ln\sigma_{g2})^2]$

Or:

$MMD_1/MMD_2 = \exp[-3/2(\ln\sigma_{g2})^2]$

---

It is advantageous to calculate the change in the MMD as the GSD changes. Solving for $MMD_2$ as a function of $MMD_1$ and the new $GSD_2$ yields:

$$MMD_2 = MMD_1/\exp[-3/2(\ln \sigma_{g2})^2] \text{ for a } \sigma_{g1}=1$$

To calculate $MMD_1$, divide the compound's mass into the number of particles and then, calculate its diameter using the density of the compound.

$$MMD_1 = (6C/pNV)^{1/3} \text{ for an aerosol with a GSD of 1}$$

Where:
C=the mass of the compound in gm's
ρ=Density in gm/cc (as before)
N=Number concentration in particles/cc (as before)
V=volume of the mixing gas in cc
Insertion of $MMD_1$ into the above equation leads to:

$$MMD_2 = (6C/pNV\pi)^{1/3}/[\exp[-3/2(\ln \sigma_{g2})^2], \text{ measured in centimeters.}$$

A resultant MMD can be calculated from the number concentration, the mass of the compound, the compound density, the volume of the mixing gas, and the GSD of the aerosol.

The required vaporization rate depends on the particle size one wishes to create. If the particle size is in the 10 nm to 100 nm range, then the compound, once vaporized, must be mixed, in most cases, into the largest possible volume of air. This volume of air is determined from lung physiology and can be assumed to have a reasonable upper limit of 2 liters. If the volume of air is limited to below 2 liters (e.g., 500 cc), too large a particle will result unless the dose is exceedingly small (e.g., less than 50 μg).

In the 10 nm to 100 nm range, doses of 1-2 mg are possible. If this dose is mixed into 2 liters of air, which will be inhaled in 1-2 seconds, the required, desired vaporization rate is in the range of about 0.5 to about 2 mg/second.

The first example of the present invention is shown in FIG. 1 and is the basic device through which the principles cited above have been demonstrated in the laboratory. This device is described in detail in the EXAMPLES.

Figure 9:
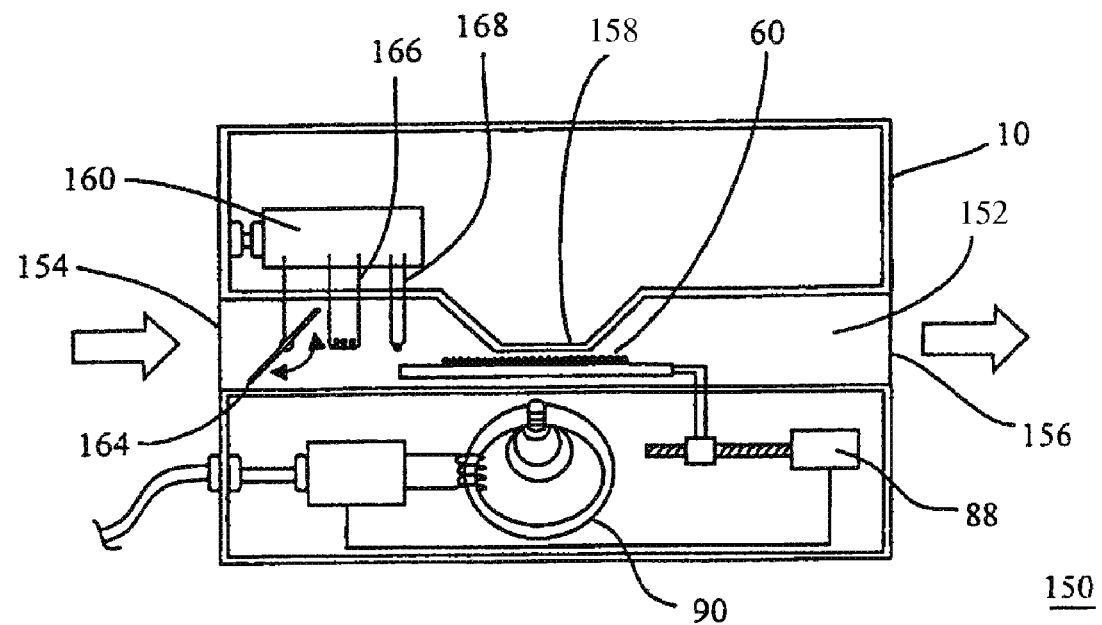
FIG. 9 is a schematic side view of a second example of the present invention using a venturi tube.

In the second example of the present invention shown in FIG. 9, the use of a reduced airway cross section increases the speed of the air across the compound's surface to about 10 meters/second. If complete mixing is to happen within 1 millisecond, then the distance the gas and vaporized mixture must travel to achieve complete mixing must be no longer than 10 millimeters. However, it is more desirable for complete mixing to happen before the compound has aggregated to a larger size, so a desirable mixing distance is typically about 1 millimeter or less.

In the fourth example of the present invention shown in FIGS. 10-13, an aerosol having particles with an MMAD in the 10 nm to 100 nm range is generated by allowing air to sweep over a thin film of the compound during the heating process. This allows the compound to become vaporized at a lower temperature due to the lowering of the partial pressure of the compound near the surface of the film.

Figure 19:
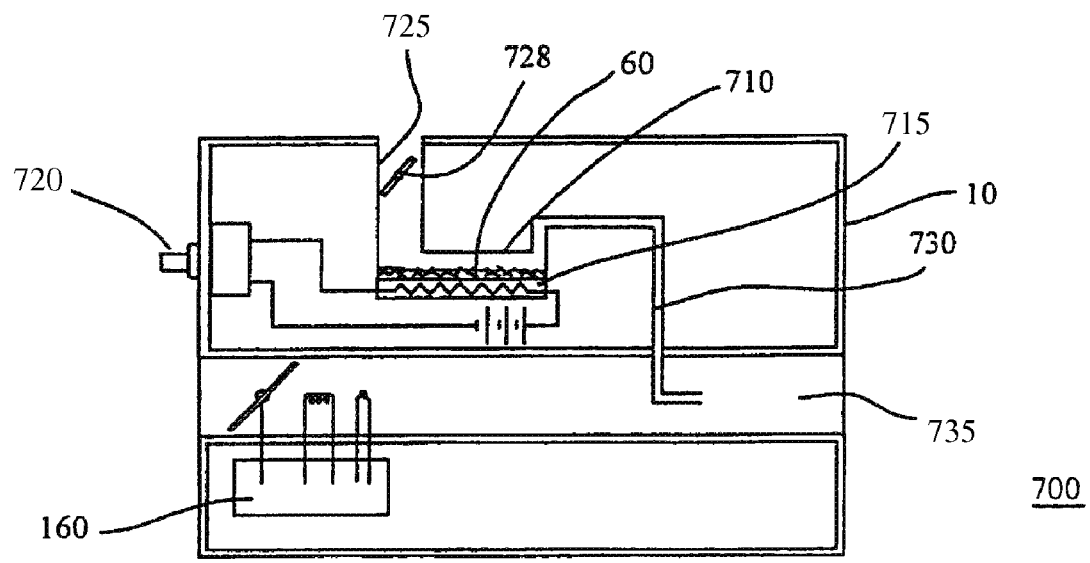
FIG. 19 is a schematic side view of an eighth example of the present invention referred to herein as the "oven device"

The fifth example shown in FIG. 14, the sixth example shown in FIGS. 15 and 16, and the eighth example shown in FIG. 19 overcome a problem with certain compounds that react rapidly with oxygen at elevated temperatures. To solve this problem, the compound is heated in an expandable container (fourth example), a small container housing under a vacuum or containing a small amount, e.g., about 1 to about 10 ml, of an inert gas (fifth example). Once a compound is vaporized and mixed with an inert gas while the gaseous mixture is maintained at a temperature sufficient to keep the compound in its vaporized state, the gaseous mixture is then injected into an air stream. The volume of inert gas can also be re-circulated over the surface of the heated compound to aid in its vaporization as shown in FIG. 16. In the seventh example, the compound is introduced into the gas as a pure vapor. This involves vaporizing the compound in an oven or other container and then injecting the vapor into an air or other gas stream through one or more mixing nozzles.

Figure 17:
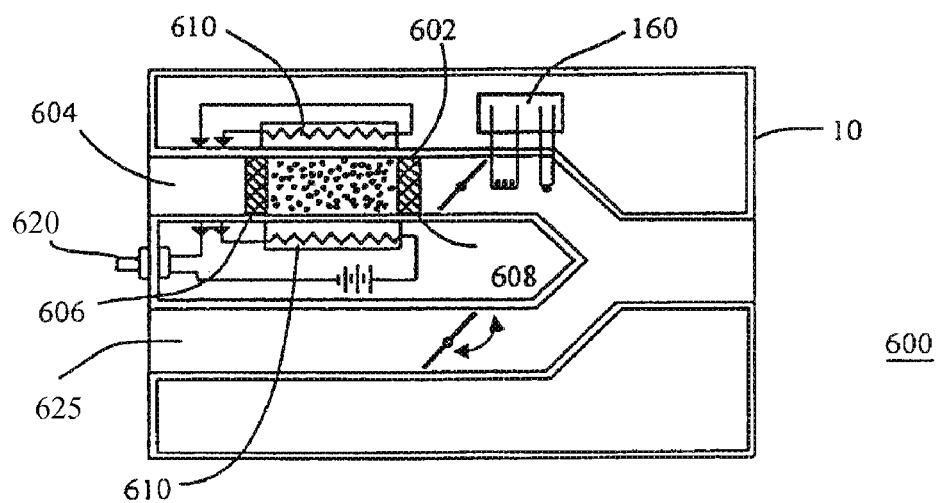
FIG. 17 is a schematic side view of a seventh example of the present invention using a tube containing particles coated with the compound.

In the sixth example shown in FIGS. 17-18, gas is passed through a first tube and over discrete substrate particles, having a large surface area to mass ratio, and coated with the compound. The particles are heated as shown in FIG. 17 to vaporize the compound, or the gas is heated and the heated gas vaporizes the compound as shown in FIG. 18. The gaseous mixture from the first tube is combined with the gas passing through second tube to rapidly cool the mixture before administering it to a patient.

Figure 20:
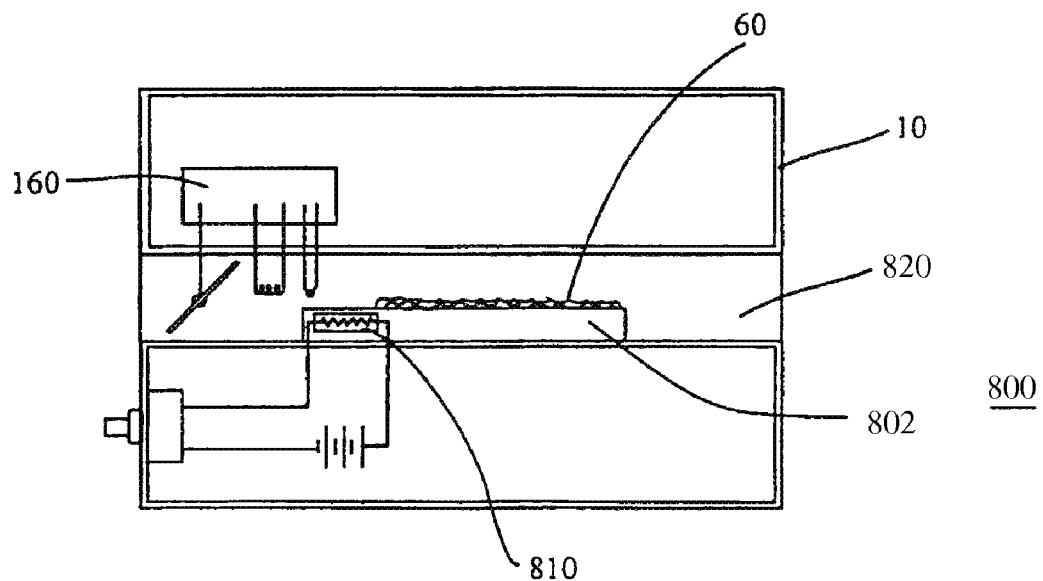
FIG. 20 is a schematic side view of an ninth example of the present invention using gradient heating.

The eighth example shown in FIG. 20 is a thermal gradient device that is similar to device 1 used in the laboratory experiments. This example also has a moving heating zone without any moving parts, accomplished by establishing a heat gradient that transverses from one end of the device to the other over time. As the heating zone moves, exposed portions of the compound are sequentially heated and vaporized. In this manner the vaporized compound can be introduced into a gas stream over time.

Figure 21:
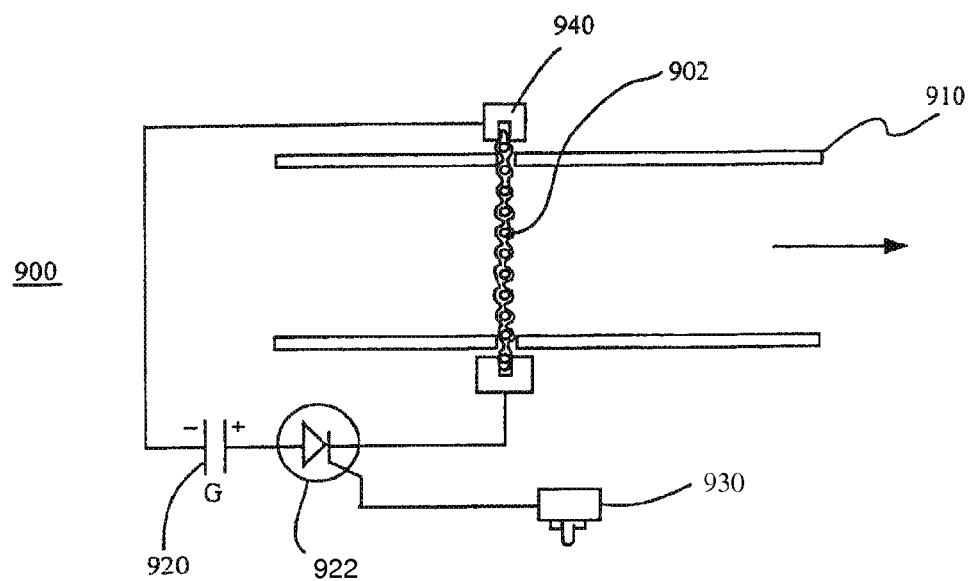
FIG. 21 is a schematic side view of a tenth example of the present invention using a fine mesh screen coated with the compound.
Figure 22:
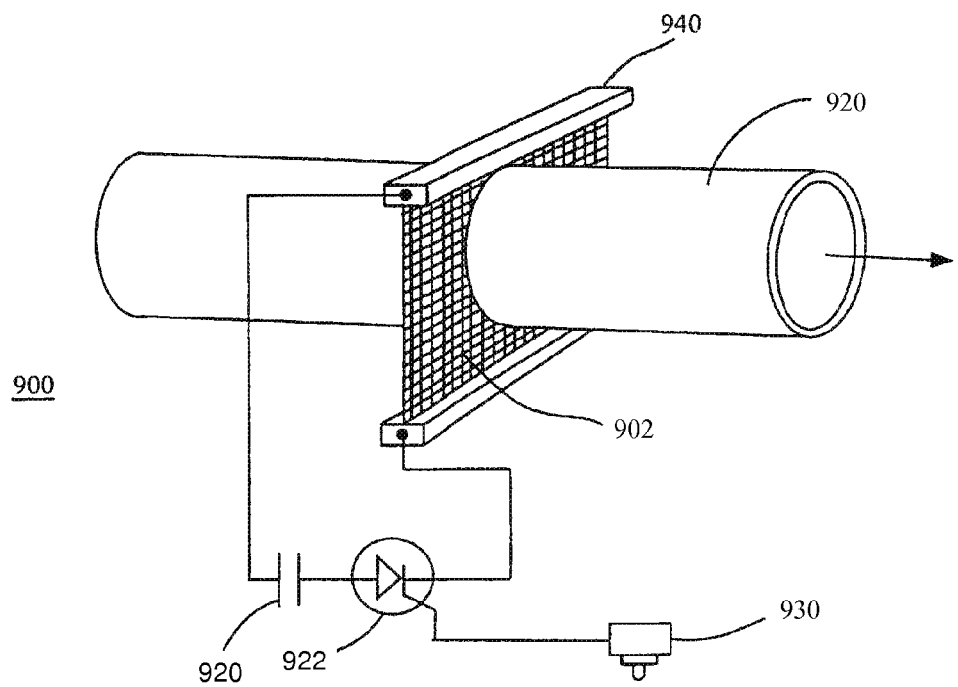
FIG. 22 is a top, right end and front perspective view of the example shown in FIG. 21.

The ninth example shown in FIGS. 21-22 is the screen device and is preferred for generating a aerosols containing particles with an MMAD greater than 100 nm. In this example, air is channeled through a fine mesh screen upon which the drug to be administered to the patient has been deposited.

The examples above can create aerosols without significant drug decomposition. This is accomplished while maintaining a required vaporization rate for particle size control by employing a short duration heating cycle. An airflow over the surface of the compound is established such that when the compound is heated and reaches the temperature where vaporization is first possible, the resulting compound vapors will immediately cool in the air. In the preferred examples, this is accomplished by extending the increased velocity and mixing region over an area that is larger than the heating zone region. As a result, precise control of temperature is not necessary since the compound vaporizes the instant its vaporization temperature is reached. Additionally because mixing is also present at the point of vaporization, cooling is accomplished quickly upon vaporization.

Application of the present invention to human inhalation drug delivery must accommodate constraints of the human body and breathing physiology. Many studies of particle deposition in the lung have been conducted in the fields of public health, environmental toxicology and radiation safety. Most of the models and the in vivo data collected from those studies, relate to the exposure of people to aerosols homogeneously distributed in the air that they breathe, where the subject does nothing actively to minimize or maximize particle deposition in the lung. The International Commission On Radiological Protection (ICRP) models are examples of this. (See James A C, Stahlhofen W, Rudolph G, Egan M J, Nixon W, Gehr P, Briant J K, *The respiratory tract deposition model proposed by the ICRP Task Group, Radiation Protection Dosimetry,* 1991; vol. 38: pgs. 157-168).

However, in the field of aerosol drug delivery, a patient is directed to breathe in a way that maximizes deposition of the drug in the lung. This kind of breathing usually involves a full exhalation, followed by a deep inhalation sometimes at a prescribed inhalation flow rate range, e.g., about 10 to about 150 liters/minute, followed by a breath hold of several seconds. In addition, ideally, the aerosol is not uniformly distributed in the air being inhaled, but is loaded into the early part of the breath as a bolus of aerosol, followed by a volume of clean air so that the aerosol is drawn into the alveoli and flushed out of the conductive airways, bronchi and trachea by the volume of clean air that follows. A typical deep adult human breath has a volume of about 2 to 5 liters. In order to ensure consistent delivery in the whole population of adult patients, delivery of the drug bolus should be completed in the first 1-1½ liters or so of inhaled air.

As a result of the constraints of human inhalation drug delivery, a compound should be vaporized in a minimum amount of time, preferably no greater than 1 to 2 seconds. As discussed earlier, it is also advantageous, to keep the temperature of vaporization at a minimum. In order for a compound to be vaporized in 2 seconds or less and for the temperature to be kept at a minimum, rapid air movement, in the range of about 10 to about 120 liters/minute, should flow across the surface of the compound.

The following parameters are optimal in using a device of the present invention, due to human lung physiology, the physics of particle growth, and the physical chemistry of the desirable compounds:

(1) The compound should to be vaporized over approximately 1 to 2 seconds for creation of particles in the ultra fine range.

(2) The compound should to be raised to the vaporization temperature as rapidly as possible.

(3) The compound, once vaporized, should be cooled as quickly as possible.

(4) The compound should be raised to the maximum temperature for a minimum duration of time to minimize decomposition.

(5) The air or other gas should be moved rapidly across the surface of the compound to achieve the maximum rate of vaporization.

(6) The heating of the air or other gas should be kept to a minimum, i.e., an increase of temperature of no greater than about 15° C. above ambient.

(7) The compound should be mixed into the air or other gas at a consistent rate to have a consistent and repeatable particle size.

(8) As the gas speed increases across the compound being vaporized, the cross sectional area through the device should decrease. Furthermore, as the surface area of the compound increases the heating of the gas increases.

The parameters of the design for one of the examples shown in FIGS. 2-5, 7 and 8 are the result of meeting and balancing the competing requirements listed above. One especially important requirement for an aerosol containing particles with an MMAD between 10 nm and 100 nm is that a compound, while needing to be vaporized within at least a 1-second period, also needs to have each portion of the compound exposed to a heat-up period that is as brief as possible. In this example, the compound is deposited onto a foil substrate and an alternating magnetic field is swept along a foil substrate heating the substrate such that the compound is vaporized sequentially over no more than about a one second period of time. Because of the sweeping action of the magnetic field, each segment of the compound has a heat-up time that is much less than one second.

In the example noted directly above, the compound is laid down on a thin metallic foil. In one of the examples set forth below, stainless steel (alloy of 302, 304, or 316) was used in which the surface was treated to produce a rough texture. Other foil materials can be used, but it is important that the surface and texture of the material is such that it is "wetted" by the compound when the compound is in its liquid phase, otherwise it is possible for the liquid compound to "ball" up which would defeat the design of the device and significantly change the volatilizing parameters. If the liquid compound "balls" up, the compound can be blown into and picked up by the airflow without ever vaporizing. This leads to delivery of a particle size that is uncontrolled and undesirable.

Stainless steel has advantages over materials like aluminum because it has a lower thermal conductivity value, without an appreciable increase in thermal mass. Low thermal conductivity is helpful because heat generated by the process needs to remain in the immediate area of interest.

EXAMPLES

The following examples further illustrate the method and various examples of the present invention. These examples are for illustrative purposes and are not meant to limit the scope of the claims in any way.

Example 1

In Vivo Results Using Example 1

In this example, example 1, was designed to deliver an experimental dose of fentanyl between 20 µg and 500 µg, in a range of ultra fine particle sizes, in about 800 cc of air to a 10 kg dog. The lung volume of each dog under experimentation was approximately 600-700 cc and the device was designed to deliver the compound to the lung in the first half of the inhalation. Because of the value of these parameters, device 1 in this experiment can be considered a ¼ scale device for administering a dose to a human. It is believed that scaling the device to work for human subjects involves mainly increasing the airflow through the device. The time frame of the introduction of the compound into the heating/vaporization/mixing zone was set such that the compound vaporized into a volume of air that was suitable for both the volume required by dog lung anatomy (600-700 cc) and the volume needed to control the ratio of the compound to the air.

The following was the sequence of events that took place during each operation:

1. At the beginning of the run, the operator triggered inhalation controller 30 to start monitoring data from pressure transducer 240 and input flow meter 4.

2. Controller 30 signaled controller 20 to start example 1 and to begin collecting data from the two temperature sensors and flow meter 4.

3. After a pre-programmed delay, example 1 initiated the generation of the aerosol. (Note: there was a delay of about 0.4 seconds between the start of the controller 30 and the start of aerosol generation.)

4. After an independent preprogrammed delay (from original trigger signal), controller 30 opened input valve 58 to start forced inhalation to a dog under experimentation.

5. Example 1 completed the aerosol generation during the inhalation.

6. Controller 30 monitored flow meter 4 and pressure transducer 240 throughout the inhalation and closed off flow at input valve 58 when a pre-specified volume or pressure was met. (Note: the pre-specified pressure is a safety feature to prevent injury to the subject animal. Termination of the breath at the pre-specified volume is the desirable occurrence of the experiment.)

7. After a breath hold delay (5 seconds), exhaust valve 40 was opened and the dog was allowed to exhale.

8. Exhaled aerosol was trapped on exhaust filter 40 for later analysis. Controller 30 recorded values for the following: volume dispensed, terminal pressure, duration of air pulse, and average flow rate. Controller 20 continuously recorded at millisecond resolution, input flow rate, exhaust flow rate, foil temperature, mouthpiece temperature, slide position, heater on/off time, and other internal diagnostic electrical parameters.

Three weight-matched female beagle dogs received fentanyl at a 100 µg intravenous bolus dose. The same dogs received fentanyl UF for Inhalation (100 µg aerosolized and administered as two successive activations of device 1, containing approximately 50 µg fentanyl base) at a particle size of 80 nm (MMAD). The aerosol was administered to anesthetized dogs via the system schematically represented in FIG. 1, with a target delivered volume of 600-700 ml air, followed by a 5 second breath hold. After dosing, plasma samples for pharmacokinetic analysis were obtained at various time points from 2 min to 24 hr. Fentanyl remaining in device 1 was recovered and measured. Fentanyl concentrations were measured by using a validated GC method, with a limit of detection of 0.2 ng/ml.

Plasma pharmacokinetics from this example were compared to intravenous (IV) fentanyl (100 µg) in the same dogs. Inhalation of fentanyl resulted in rapid absorption ($C_{max}$, maximum concentration in plasma, 11.6 ng/ml and $T_{max}$, maximum time, 2 min.) and high bioavailability (84%). The time course of inhaled fentanyl was nearly identical to that of IV fentanyl. Thus, fentanyl UF for inhalation had an exposure profile that was similar to that of an IV injection.

Standard non-compartmental pharmacokinetic methods were used to calculate pharmacokinetic parameters for each animal. The maximum concentration in plasma ($C_{max}$) and the maximum time it occurred ($T_{max}$) were determined by examination of the data. The area under the plasma concentration vs. time curve (AUC) was determined. The bioavailability (F) of inhaled fentanyl was determined as:

$$F=(DIV/DINHAL)*(AUCINHAL/AUCIV)$$

where D was the dose and AUC was the AUC determined to the last measurable time point.

Figure 26:
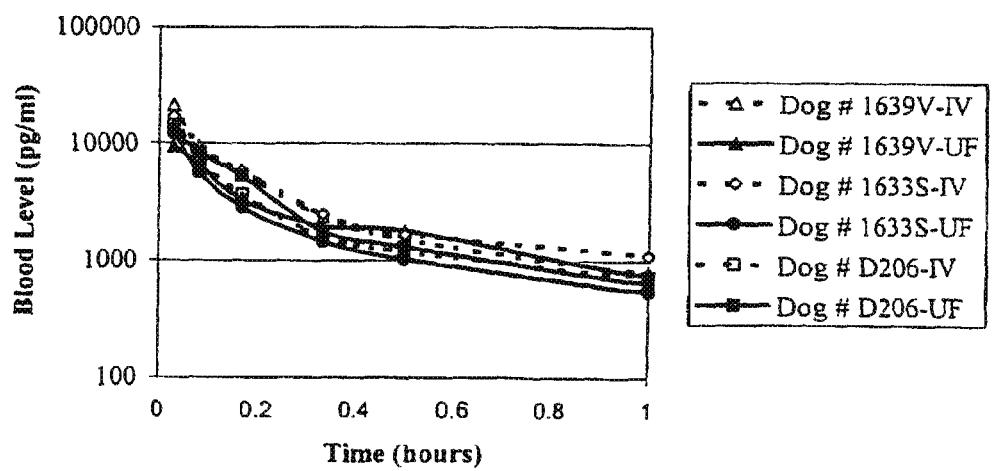
FIG. 26 is a plot of blood levels for both the IV dose and the inhalation dose administered to various dogs during the experiments using the system shown in FIG. 1.
Figure 27:
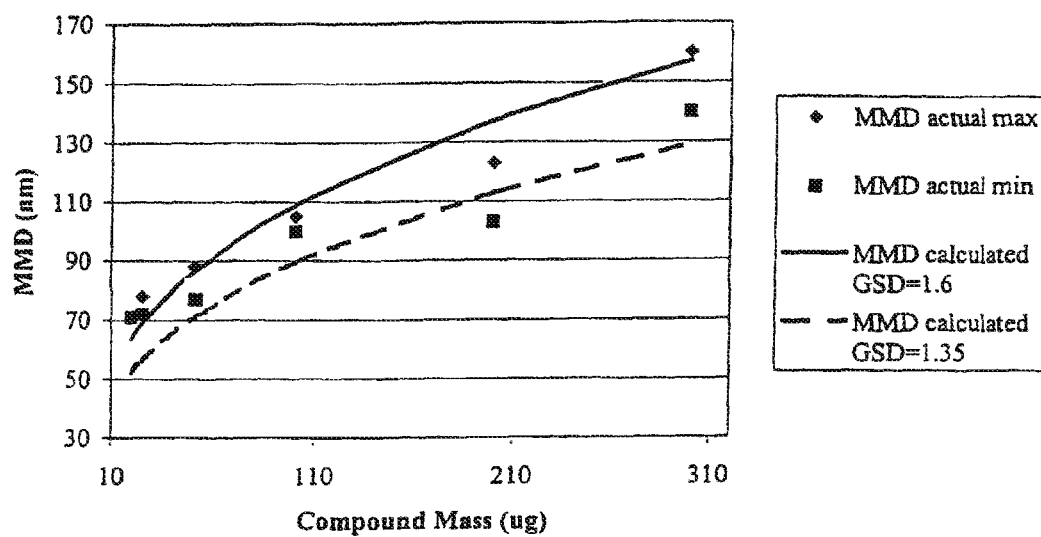
FIG. 27 is a plot of calculated and experimental mass median diameter (MMD) versus compound mass in the range of 10 to 310 µg.
Figure 28:
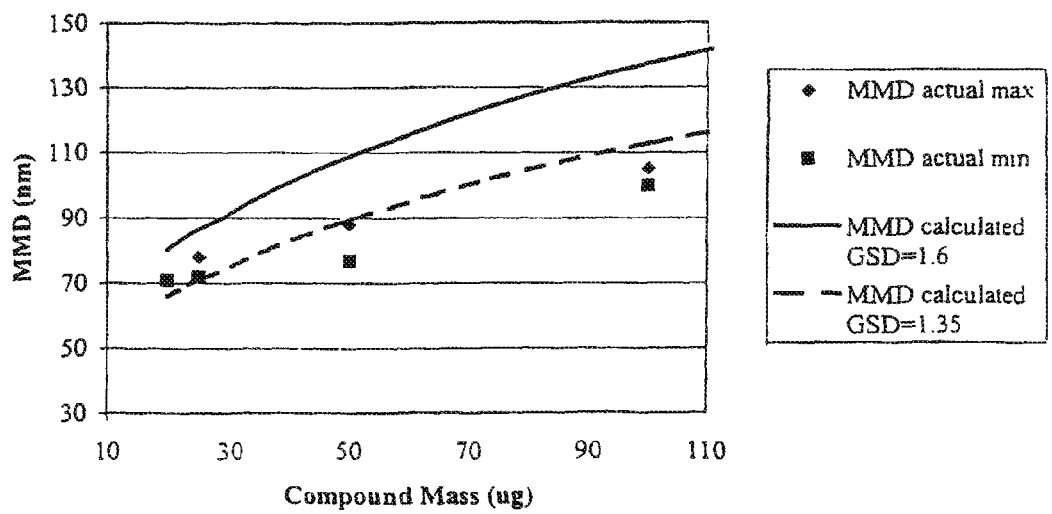
FIG. 28 is a plot of calculated and experimental MMD versus compound mass in the range of 10 to 310 µg.

FIG. 26 plots the data obtained on the blood levels, by dog, for both the IV doses and the inhalation doses using device 1 as described above under Example 1.

The fentanyl aerosol was rapidly absorbed, with the same $T_{max}$ (2 min, the earliest time point) observed for both routes of administration. The maximum plasma concentration of fentanyl aerosol (11.6±1.9 ng/ml) was nearly two-thirds that of IV fentanyl (17.6±3.6 ng/ml). Plasma concentrations fell below the assay limit of quantitation by 6-8 hr after IV administration and by 3-4 hr after aerosol inhalation. Bioavailability calculations were based on the AUC's observed to the last measurable time point for the inhalation administration. Bioavailability for the inhalation study was 84% based on the nominal (uncorrected) fentanyl dose.

The mean plasma elimination half-life was similar after IV (75.4 min) and inhalation dose. Distribution phase half-lives (3-4 min) were also similar after both routes of administration. The inter-animal variability of pharmacokinetic parameters after the inhalation dose was low, with relative standard deviations (RSD<25%) lower than those observed for IV administration.

Example 2

In Vitro Results Using Example 1

Table 2 below summarizes the data collected from use of example 1 for in vitro testing of fentanyl. Particle size was measured with a Moudi cascade impactor.

TABLE 2

| Compound Mass (ug) | Mixing air volume (cc) | MMAD (nm) | GSD |
|---|---|---|---|
| 20 | 400 | 71 | 1.9 |
| 25 | 400 | 72-78 | 1.7-1.8 |
| 50 | 400 | 77-88 | 1.7-185 |
| 100 | 400 | 100-105 | 1.4-1.8 |
| 200 | 400 | 103-123 | 1.6-1.9 |
| 300 | 400 | 140-160 | 1.8-2.1 |

Example 3

Use of Example 1 to Make Fine Aerosol Particles

In this example, example 1 was slightly modified and the flow rate changed, as discussed below, to make a fine aerosol in the 1 to 3 micron particle size range.

Airway section 140 was removed and the air channel heating/vaporization zone 70 was changed. An airway insert (not shown) had a "roof" that was 0.25 inches above the foil. There were no mixing rods as rapid mixing was not desirable in this example. Because of these two device changes, there was much less mixing with the air, thus the vapor/aerosol cloud was mixed with less air and produced a larger particle size aerosol. The airflow rate was reduced 1 liter/minute in this example. Again, this allowed the vapor to be mixed with much less air, resulting in the larger particle size aerosol.

Some operational problems with high compound loading on foil 64 in example 1 were encountered. The compound tested, dioctyl phthalate (DOP), was an oil and during the aerosolization process, a substantial quantity was blown downwind and not aerosolized. Three additional design alternatives were made to address this issue, involving changes to the substrate surface that the compound was deposited on. In the three alternatives, the substrate was made to "hold" the compound through the use of texture. They were: a) texturing the foil; b) adding a stainless steel screen on top of the foil; and, c) replacing the foil with a fine stainless steel screen.

The results from this example are set forth below in Table 3 below:

TABLE 3

| Substrate Type | MMAD, microns | GSD | Emitted Dose, ug |
|---|---|---|---|
| Textured foil | 1.49 microns | 1.9 | 97 |
| Textured foil | 2.70 microns | 1.95 | 824 |
| Fine screen alone | 1.59 microns | 1.8 | 441 |

TABLE 3-continued

| Substrate Type | MMAD, microns | GSD | Emitted Dose, ug |
|---|---|---|---|
| Fine screen alone | 1.66 microns | 1.8 | 530 |
| Screen on Foil | 2.42 microns | 2.2 | 482 |

As shown above, a fine particle size can be made with device 1 merely by changing the ratio of the compound to the mixing air.

Example 4

In Vitro Results Using Example 700

A tank was partially filled with DOP and placed inside an oven (not shown) having an inlet and an outlet. DOP was used as the test compound. The tank was purged with helium prior to heating the tank and its contents to a temperature of 350° C. Helium was pumped through the tank and used to carry the DOP vapor out of the outlet. The gaseous mixture of helium and vaporized compound 60 was introduced into different size mixing tubes through a nozzle. Each of the tubes had air moving through them at 14 liters/minute. The nozzle was perpendicular to the flow direction. After this gaseous mixture was mixed with the air, the resulting aerosol was introduced into a parallel flow diffusion battery for particle size analysis. Results are set forth in Table 4 below.

TABLE 4

| Mixing tube size (ID) | MMAD | GSD |
|---|---|---|
| 4.8 mm | 65 nm | 1.3 |
| 14 mm | 516 nm | 3.3 |

As can be seen above, as the tube diameter became larger so did the particle size. Additionally, as the diameter became larger, the GSD also became larger. As the tube becomes larger, it is believed that the vaporized gas is introduced into a smaller segment of the mixing gas because the gas is being introduced as a point source leading to uneven mixing, which results in a large GSD.

Example 5

In Vitro Results Using Example 800

To demonstrate effectiveness of example 800, a 4-inch long piece of aluminum was fitted with a 150-watt cartridge heater at one end. The heater was powered with a variac AC power transformer. The thickness of the aluminum was designed to ensure that heat would transverse from one end of the aluminum to the other in approximately 30 seconds.

On the topside of the aluminum, an indentation was machined to hold the compound and to hold one of two top covers. The indentation for the compound was approximately 3.5 inches long and 0.4 inches wide. The indentation was 0.025 inches deep, and was filled with 1 mg of DOP.

The first top consisted of a sheet of flat glass placed 0.04 inches above the heated surface, creating an airway. At the exit end an outlet was fitted allowing the air to be drawn into an analytical measurement device. Air was made to flow through the airway at a rate of 15 liters/minute.

In the second configuration, the top was replaced with a half cylinder made of glass. This increased the cross sectional area of the airway by an order of magnitude.

Particle size was measured with both configurations and shown to be affected by the cross sectional area of the airway.

Results from the thermal gradient test are set forth in Table 5 below:

TABLE 5

| Cover size and cross-section | MMAD | GSD |
|---|---|---|
| Small | 92 nm | 1.4 |
| Big | 650 nm | unknown |

As shown above, the results confirm that as the cross section becomes larger, so does the particle size.

Example 6

In Vitro Results Using Example 900

In this example for producing aerosols, airway passage 910 was constructed from 18 mm diameter glass tubing. However, the passage can be made in any shape with a comparable cross-sectional area and out of any suitable material. The screen size, mesh, and the amount of compound were chosen in this example so that a gas could pass through the screen without interference once the compound had been deposited on it.

Because the internal resistance of the screen was low, i.e., between 0.01 and 0.2 ohms, the discharge rate (the RC time constant) of the capacitor was rapid, and on the order of a few milliseconds, i.e. less than 20 milliseconds, preferably in the range of about 2 to about 10 milliseconds. Upon discharge of capacitor 902 and the subsequent heating of screen 902, the deposited compound was rapidly vaporized. Because air moved through screen 902, the vaporized compound rapidly mixed with air and cooled.

The compound was deposited onto the fine stainless steel screen, e.g., 200 mesh, made from 316 stainless steel, having measurements of 2.54 cm.×2.54 cm. The current from the capacitor was passed between one edge and another. It was not necessary to heat the screen to temperatures comparable to the thin foil in Example 1, because the compound vaporized at a lower temperature due to the rapid air movement. Rapid air movement allowed the compound to vaporize at a lower vapor pressure, since airflow constantly removed compound vapors from the surface as soon as they were formed. Thus, the compound vaporized at a lower temperature without decomposition.

Deposition of the compound onto the screen was accomplished by mixing the compound with an organic solvent until the compound dissolved. The resulting solution was then applied to the fine stainless steel screen 902 and the solvent was allowed to evaporate. The screen was then inserted into holder 940 that electrically connected two sides of screen 902 to the power circuit described above.

A 10,000 mF capacitor was discharged while the gas was passing through screen 902. The rapid heat up of the screen resulted in a rapid vaporization of the compound into the gas. Thus the resulting vaporized compound was mixed into a small volume of the gas. Because the ratio of the mass of the compound to the volume of the mixing gas was large, a fine (1-3 micron diameter) particle aerosol was made.

Example 7

Flash Device for Forming Aerosols

A high-power flashcube (GE or Sylvania), which can produce 300-400 J of energy, was inserted into an anodized aluminum tube. The flashcube/tube assembly was dipped into an organic solution containing a drug and quickly removed. Evaporation of residual solvent from the assembly was performed by placing it into a vacuum chamber for 30 min. This left a film of drug coated on the exterior surface of the aluminum tube. The flashbulb assembly was electrically connected to two 1.5 V batteries and a switch using copper wires and then enclosed in a sealed, glass vial. Ignition of the flashbulb was performed by momentarily turning on the switch between the flashbulb and batteries. After ignition, the vial was kept closed for 30 minutes such that particles of volatilized drug coagulated and condensed on the inside surface of the vial. Analysis of the aerosol involved rinsing the vial with 5 mL of acetonitrile and injecting a sample of the organic solution into an HPLC.

Measurement with a fast thermocouple indicated that the aluminum tube heated up to 600° C. in 50 milliseconds. This translates into a heating rate of 12,000°/s.

One of ordinary skill in the art would understand that the experimental device detailed above could be transformed into an inhalation delivery device by excluding the sealed vial and including a housing to contain the assembly and electrical components. The housing would contain an air inlet and a mouthpiece such that, when drug volatilization occurred, an inhaled breath would carry the formed aerosol into the lungs of a subject.

Example 8

Relationship Between Film Thickness and Aerosol Purity

Sildenafil was dissolved in a minimal amount of dichloromethane. The resulting solution was coated onto a piece of pure aluminum foil, and the residual solvent was allowed to evaporate. The coated foil was placed on an aluminum block that had been preheated to 275° using a hot plate. A pyrex beaker was synchronously placed over the foil, and the coated material was allowed to vaporize for 1 min. The beaker was removed, and the adsorbed aerosol was extracted using dichloromethane. HPLC analysis (250 nm) of an aliquot of the extract provided purity data for the aerosol. Using this procedure the following data were obtained: 3.4μ thickness, 84.8% purity; 3.3μ thickness 80.1% purity; 1.6μ thickness, 89.8% purity; 0.8μ thickness, 93.8% purity; 0.78μ thickness, 91.6% purity; 0.36μ thickness, 98.0% purity; 0.34μ thickness, 98.6% purity; 0.29μ thickness, 97.6% purity; and, 0.1μ, 100% purity.

Example 9

General Procedure for Screening Drugs to Determine Aerosolization Preferability

Drug (1 mg) is dissolved or suspended in a minimal amount of solvent (e.g., dichloromethane or methanol). The solution or suspension is pipeted onto the middle portion of a 3 cm by 3 cm piece of aluminum foil. The coated foil is wrapped around the end of a 1½ cm diameter vial and secured with parafilm. A hot plate is preheated to approximately 300° C., and the vial is placed on it foil side down. The vial is left on the hotplate for 10 s after volatilization or decomposition has begun. After removal from the hotplate, the vial is allowed to cool to room temperature. The foil is removed, and the vial is extracted with dichloromethane followed by saturated aqueous $NaHCO_3$. The organic and aqueous extracts are shaken together, separated, and the organic extract is dried over $Na_2SO_4$. An aliquot of the organic solution is removed and injected into a reverse-phase HPLC with detection by absorption of 225 nm light. A drug is preferred for aerosolization where the purity of the drug isolated by this method is greater than 85%. Such a drug has a decomposition index less than 0.15. The decomposition index is arrived at by substracting the percent purity (i.e., 0.85) from 1.

One of ordinary skill in the art can combine the foregoing embodiments or make various other embodiments and aspects of the method and device of the present invention to adapt them to specific usages and conditions. As such, these changes and modifications are properly, equitably, and intended to be, within the full range of equivalents of the following claims.

The invention claimed is:

1. A method of forming an aerosol for use in inhalation therapy comprising:
 (a) heating a substrate coated with a composition comprising a drug, thereby forming a vapor;
 (b) establishing an airflow over the surface of the coated composition during said heating; and
 (c) allowing the vapors to cool in the air flow thereby forming an aerosol comprising the drug,
 wherein a dose of the drug is vaporized in less than 1 second.

2. The method according to claim 1, wherein a dose of the drug is vaporized in less than 500 milliseconds.

3. The method according to claim 2, wherein a dose of the drug is vaporized in less than 100 milliseconds.

4. The method according to claim 3, wherein the formed aerosol is greater than 80 percent by weight of the drug.

5. The method according to claim 3, wherein the formed aerosol contains less than 5 percent by weight of drug decomposition products.

6. The method according to claim 3, wherein the formed aerosol is stable over 1 second.

7. The method according to claim 3, wherein the formed aerosol has an MMAD in the 10 nm to 100 nm range.

8. The method according to claim 3, wherein the formed aerosol has an MMAD in the 1 μm to 3 μm range.

9. The method according to claim 3, wherein the geometric standard deviation of the form aerosol is other than 1.

10. The method according to claim 3, wherein the film is less than 10 μm thick.

11. The method according to claim 10, wherein the film is less than 5 μm thick.

12. The method according to claim 10, wherein the film is between 10 nm and 5 μm thick.

13. The method according to claim 10, wherein the film is less than 3 μm thick.

14. The method according to claim 12, wherein the film is between 10 nm and 3 μm thick.

* * * * *